United States Patent [19]

Hamprecht et al.

[11] 4,298,731

[45] Nov. 3, 1981

[54] BENZOTHIADIAZINE COMPOUNDS

[75] Inventors: Gerhard Hamprecht, Mannheim; Gerd Stubenrauch, Ludwigshafen; Hans Urbach, Lampertheim; Bruno Wuerzer, Limburgerhof, all of Fed. Rep. of Germany

[73] Assignee: BASF Aktiengesellschaft, Fed. Rep. of Germany

[21] Appl. No.: 851,826

[22] Filed: Nov. 16, 1977

[30] Foreign Application Priority Data

Dec. 11, 1976 [DE] Fed. Rep. of Germany ....... 2656290

[51] Int. Cl.$^3$ ............................................ C07D 285/16
[52] U.S. Cl. ............................................. 544/11; 71/91
[58] Field of Search ........................ 544/11; 71/90, 91

[56] References Cited

U.S. PATENT DOCUMENTS

| | | | |
|---|---|---|---|
| 3,217,001 | 11/1965 | Santilli et al. | 544/11 |
| 3,940,389 | 2/1976 | McKendry et al. | 544/11 |
| 3,997,531 | 12/1976 | Fischer et al. | 544/11 |
| 4,051,130 | 9/1977 | McKendry et al. | 544/11 |
| 4,054,440 | 10/1977 | McKendry et al. | 544/11 |
| 4,075,004 | 2/1978 | Hamprecht et al. | 544/11 |
| 4,113,939 | 9/1978 | Fischer et al. | 544/11 |
| 4,139,700 | 2/1979 | Kloek | 544/11 |
| 4,158,559 | 6/1979 | Stubenrauch et al. | 544/11 |
| 4,208,514 | 6/1980 | McKendry et al. | 544/11 |

FOREIGN PATENT DOCUMENTS 1120456 12/1961 Fed. Rep. of Germany ........ 544/11

OTHER PUBLICATIONS

Sadohara et al., Chemical Abstracts, vol. 86, entry 66858 (1977).

*Primary Examiner*—John M. Ford
*Attorney, Agent, or Firm*—Lee & Witherspoon

[57] ABSTRACT

New and valuable substituted 2,1,3-benzothiadiazine compounds having a herbicidal action, herbicides containing these compounds as active ingredients, processes for controlling the growth of unwanted plants with these compounds, and methods of manufacturing them.

8 Claims, No Drawings

BENZOTHIADIAZINE COMPOUNDS

The present invention relates to new and valuable substituted 2,1,3-benzothiadiazine compounds having a herbicidal action, herbicides containing these compounds as active ingredients, processes for controlling the growth of unwanted plants with these compounds, and methods of manufacturing them.

It is known that 3-isopropyl-2,1,3-benzothiadiazin-(4)-one-2,2-dioxide has a selective herbicidal action (German Pat. No. 1,542,836). Other herbicides from this class of compounds are also known which may be used for removing unwanted plants from a number of crop plants (German Laid-Open Applications DOS Nos. 2,444,383; 2,443,901; and 2,458,343).

We have now found that compounds of the formula

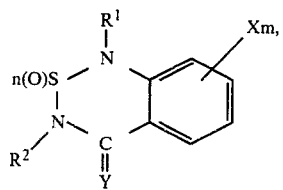

where $R^1$ and $R^2$ are identical or different and each denotes alkyl, cycloalkyl, alkenyl, alkynyl, haloalkenyl, haloalkynyl, alkoxycarboalkyl, alkoxycarboalkenyl, dialkylketone, azidoalkyl, thiocyanatoalkyl, cyanoalkyl, benzyl, unsubstituted or substituted carbamidoalkyl, unsubstituted or halo- or methyl-substituted aryl, and the following radicals, the final alkyl in each case having more than 1 carbon atom; unsubstituted or substituted haloalkyl or alkylmercaptoalkyl, arylmercaptoalkyl and alkoxyalkyl; $R^1$ further denotes hydroxyalkyl having more than 1 carbon atom or methyl substituted by O-alkyl-N-alkylaminophosphorothio, O,O-dialkylphosphoro, O,O,O-trialkylphosphinylimino, alkoxydithiocarbonyl, alkoxycarbamoyl, alkoxycarbamoyl-N-aryl, alkylsulfinyl, alkylsulfonyl, thiocarbamido, isothiuronium hydrochloride,

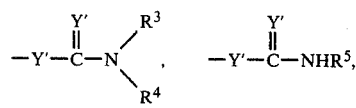

or unsubstituted or substituted acylamido, diacylamido or isoxazole; each X independently denotes halogen, $-NO_2$, lower alkyl, halogen lower alkyl, cycloalkyl, aryl, $-SCN$, $-CN$, $-CO_2R^3$,

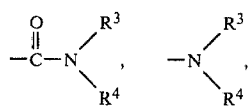

$-Y''R^4$, $-SO_2R^3$, $-SO_2OR^3$,

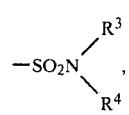

$-CCl_3$, $-CF_3$, $-CH_2-O-CH_3$,

or $-Y'-CF_2C(Z)_3$, m denotes one of the integers 0, 1, 2, 3 and 4 an n denotes one of the integers 1 and 2, $R^3$ denoting lower alkyl, $R^4$ denoting lower alkyl or hydrogen, $R^5$ denoting lower alkyl or aryl, each Y, Y' and Y'' independently denoting oxygen or sulfur, and each Z independently denoting hydrogen, fluoro, bromo or chloro, enable unwanted broadleaved plants and Cyperaceae to be controlled beyond the known range for this class of compounds, in more crops and with much less risk than was hitherto the case.

The compounds according to the invention have better solubility in nonpolar hydrocarbons, e.g., vegetable or animal oils, and therefore offer technological advantages in the manufacture and application of the compounds as herbicidal agents. The compounds of the invention are thus a considerable enrichment of the art.

The new benzothiadiazine compounds are obtained by reacting 2,1,3-benzothiadiazine compounds of the formula

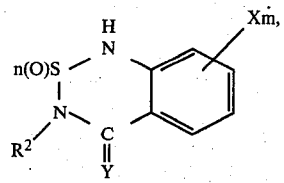

where $R^2$, Y, X, m and n have the above meanings, with
  (a) a halogen compound of the formula $$Hal-R^1 \qquad II,$$

where $R^1$ has the above meanings and Hal denotes a halogen atom, or
  (b) a sulfate of the formula $$SO_2(OR^1)_2 \qquad III,$$

or
  (c) a sulfone ester of the formula $$ArSO_2OR^1 \qquad IV,$$

where $R^1$ has the above meanings and Ar denotes aryl, in the presence or absence of an acid binder and of a solvent, or by reacting salts of compounds of the formula I with a halogen compound of the formula II or a sulfate of the formula III or a sulfone ester of the formula IV in the presence of a solvent, or by reacting benzothiadiazine compounds of the formula

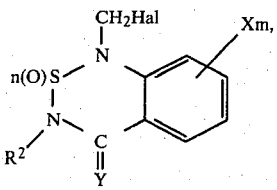

where $R^2$, Y, X, m and n have the above meanings and Hal denotes a halogen atom, with a salt of hydrocyanic acid, thiocyanic acid, hydrazoic acid, unsubstituted or substituted carbamic or thiocarbamic acid, alkoxydithiocarbamic acid, O-alkyl-N-alkylaminothiophosphoric acid, an O,O,O-trialkylphosphite or thiourea, or by reacting compounds of the formula

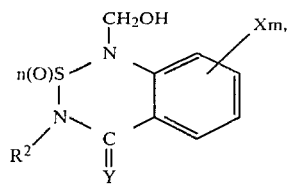

where $R^2$, Y, X, m and n have the above meanings, with an isocyanate of the formula $$O=C=N-R^5 \qquad VII,$$

where $R^5$ denotes lower alkyl or phenyl.

The reaction of starting compounds I and II is preferred.

Examples of meanings for $R^1$ and $R^2$ are methyl, ethyl, n-propyl, isopropyl, cyclopropyl, n-butyl, isobutyl, tertbutyl, cyclobutyl, n-pentyl, 2-pentyl, 3-pentyl, tert-amyl, neopentyl, 2-methylbutyl, 3-methylbutyl, 3-methyl-2-butyl, cyclopentyl, n-hexyl, 4-methyl-2-pentyl, 2,3-dimethylbutyl, 2-methyl-1-pentyl, 2-hexyl, 3-methyl-2-pentyl, 3-methylpentyl, 4-methylpentyl, 3-methyl-3-pentyl, 4,4-dimethylbutyl, cyclohexyl, heptyl, 2-heptyl, 3-heptyl, 4-heptyl, cycloheptyl, 1-octyl, 2-octyl, 3-octyl, 4-octyl, 5-octyl, 5-ethyl-2-heptyl, 2,6-dimethyl-4-heptyl, 7-ethyl-2-methyl-4-nonyl, 2,4-dimethyl-3-pentyl, 3-methyl-2-heptyl, 5-ethyl-2-nonyl, nonyl, decyl, undecyl, dodecyl, tridecyl, tetradecyl, pentadecyl, hexadecyl, heptadecyl, octadecyl, nonadecyl, eicosyl, 6-ethyl-3-decyl, 6-ethyl-3-octyl, 2-methyl-2-pentyl, 2,3-dimethyl-2-butyl, 2-methyl-2-hexyl, 3-ethyl-3-pentyl, 3-methyl-3-hexyl, 2,3-dimethylpentyl-3, 2,4-dimethyl-2-pentyl, 2,2,3-trimethyl-3-butyl, 2-methyl-2-heptyl, 4-methyl-4-heptyl, 2,4-dimethyl-2-hexyl, 2-methyl-2-octyl, 1-methyl-1-cyclopentyl, 1-methyl-1-cyclohexyl, 1-ethyl-1-cyclohexyl, chlorotert-butyl, 1,1-dichloro-2-methyl-2-propyl, 1,3-dichloro-2-methyl-2-propyl, 1-cyclohexyl-1-ethyl, 1-chloroethyl, 2-chloroethyl, 1-chloropropyl, 2-chloropropyl, 3-chloropropyl, 1-chloro-2-propyl, 2-chlorobutyl, 2-chloro-2-methyl-3-propyl, 1-fluoroethyl, 2-fluoroethyl, 2-fluoropropyl, 3-fluoropropyl, 1-fluoro-2-propyl, 2-fluorobutyl, 2-fluoro-2-methyl-3-propyl, 2-bromoethyl, 3-bromopropyl, 4-chlorobutyl, 2-chlorocyclohexyl, 1,1,1-trifluoroisopropyl, hexafluoro-2-methylisopropyl, hexafluoroisopropyl, hexachloroisopropyl, 1,2-dibromallyl, 2,2,2-trifluoroethyl, 1-chlorobutyn-2-yl-4, 3-chlorobutyn-1-yl-4, 1-chlorobuten-2-yl-4, 2,2,2-trichloroethyl, 1-chloropentyn-2-yl-4, 2,2,2-tribromoethyl, 3,4,4-trichlorobuten-3-yl-2, 1-bromo-2-propyl, 1,3-dibromo-2-propyl, 3-chlorobuten-1-yl-4, benzyl, o,m,p-toluene, o,m,p-fluorophenyl, vinyl, ethynyl, propen-1-yl, propyn-1-yl, allyl, propargyl, crotyl, butyn-2-yl-1, methallyl, buten-1-yl-3, butyn-1-yl-3, buten-1-yl-4, 2-methylbuten-1-yl-3, 2-methylbuten-2-yl-1, 2-methylbuten-2-yl-4, 3-methylbuten-1-yl-3, 3-methylbutyn-1-yl-3, 2-methylbuten-1-yl-4, 2-ethylhexen-2-yl-1, hexen-5-yl-1, undecen-10-yl-1, 1-ethynylcyclohexyl, methoxyethyl, ethoxyethyl, 3-methoxypropyl, methoxyisopropyl, 3-methoxybutyl, 1-methoxybutyl-2, ethoxytert-butyl, methoxy-tert-butyl, cyclohexoxy-tert-butyl, 2-methoxybutyl, 4-methoxybutyl, β-methylmercaptoethyl, β-ethylmercaptoethyl, 3-methylmercaptopropyl, 3-methylmercaptobutyl, 1-methylmercaptobutyl-2, methylmercapto-tert-butyl, 2-methylmercaptobutyl, 4-methylmercaptobutyl, 3-n-butoxyethyl, 2-ethoxypropyl, 3-ethoxy-2-propyl, 2-methylbutanon-2-yl-2, 2-methylpentanon-4-yl-2, 3-butanon-1-yl, 3-butanon-2-yl, 2-propanon-1-yl, 2-pentanon-1-yl, methyl acetate-2, ethyl acetate-2, methyl propionate-2, methyl propionate-3, methyl butyrate-2, methyl butyrate-3, methyl butyrate-4, methyl-(2-vinylpropionate-2), methyl-(2-vinylacetate-2), methylcarbamoylmethyl, dimethylcarbamoylmethyl, carbamoylmethyl, carbamoylethyl, α-cyanoethyl, β-cyanoethyl, γ-cyanoethyl, and β-pheylmercaptoethyl.

$R^1$ may also denote cyanomethyl, thiocyanomethyl, azidomethyl, dimethylcarbamoylthiomethyl, dimethyldithiocarbamoylmethyl, diethylcarbamoylthiomethyl, diethyldithiocarbamoylmethyl, diisopropyldithiocarbamoylmethyl, diisobutylcarbamoylthiomethyl, hexamethylenecarbamoylthiomethyl, N-ethyl-N-butylcarbamoylthiomethyl, N-ethyl-N-butyldithiocarbamoylmethyl, 2-methylhexahydroazepinecarbodithiomethyl, 2,4,4-trimethylazetidinecarbithiomethyl, 2,4,4-trimethylazetidinecarbodithiomethyl, chloroacetoamidomethyl, phthalyliminomethyl, phenylcarbamoyloxymethyl, O-ethyl-N-isopropylaminophosphorothiomethyl, methylsulfynylmethyl, ethylsulfynylmethyl, methylsulfonylmethyl, ethylsulfonylmethyl, 3-methylisoxazole-5-methyl, 3-methyl-4-chloroisoxazole-5-methyl, O,O-dimethylphosphoromethyl, O,O-diethylphosphoromethyl, thiocarbamidomethyl, methoxycarbamoyl-N-phenylmethyl, ethoxycarbamoylmethyl, p-fluorophenylcarbamoyloxymethyl, diisobutylcarbamoylthiomethyl, ethoxydithiocarbonylmethyl, isothiuronium hydrochloride methyl, O,O,O-triethylphosphynyliminomethyl, and the radicals β-hydroxyethyl, α-acetamido-β,β,β-trichloroethyl, α-formamido-β,β,β-trichloroethyl, α-[α-methoxycarbomethylthio]-acetic acid methyl ester, α-ethoxycarbamidoacetic acid, β,β,β-trichloroethyl-α-acetic acid.

The term "halogen" denotes fluorine, chlorine, bromine and iodine. The terms "lower alkyl" and "halogen lower alkyl" denote linear or branched, unsubstituted or halogen-substituted alkyl of from 1 to 6 carbon atoms.

The term "cycloalkyl" denotes for example cyclopropyl, cyclobutyl, cyclopentyl, cyclohexyl and cycloheptyl. The term "aryl" denotes phenyl and substituted phenyl such as halophenyl or tolyl.

If the starting materials are the sodium salt of 3-ethyl-2,1,3-benzothiadiazin-(4)-one-2,2-dioxide and butynyl chloride, the reaction may be represented by the following scheme:

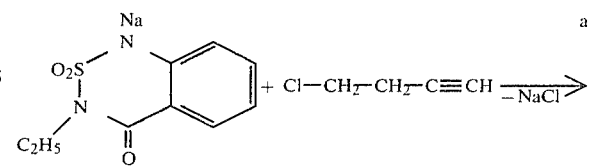

-continued

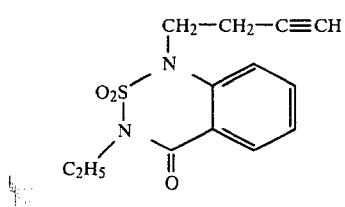

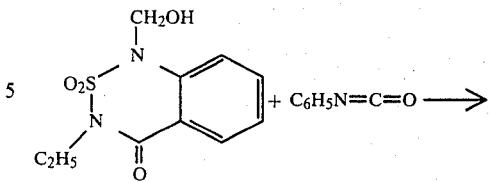

If the starting materials are 3-ethyl-2,1,3-benzo-thiadiazin-(4)-one-2,2-dioxide and dimethyl sulfate (b) or methyl p-toluenesulfonate (c), the reaction is represented by the following schemes:

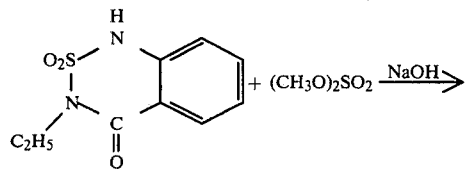   b

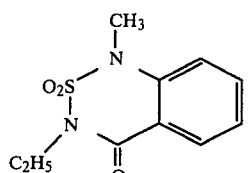

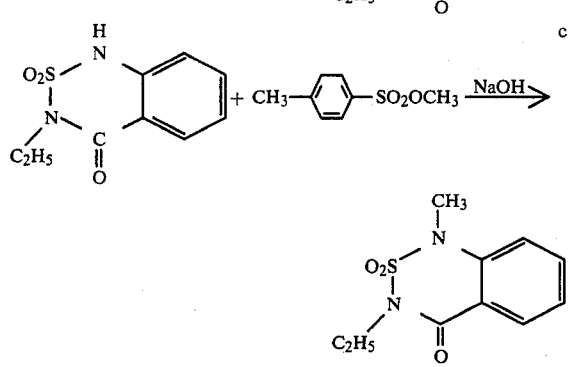   c

If the starting materials are 1-chloromethyl-3-ethyl-2,1,3-benzothiadiazin-(4)-one-2,2-dioxide and the dimethylammonium salt of dimethyldithiocarbamic acid, the reaction is represented by the following scheme:

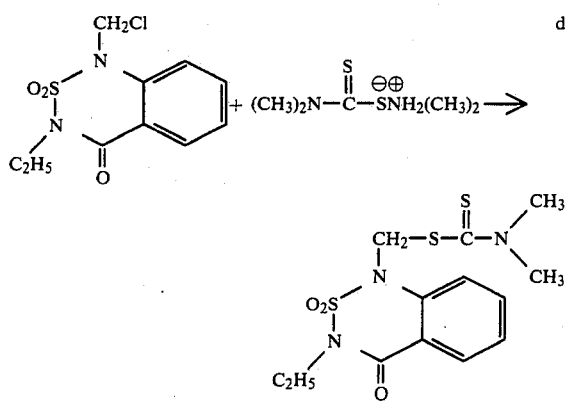   d

If the starting materials are 1-methylol-3-ethyl-2,1,3-benzothiadiazin-(4)-one-2,2,-dioxide and phenyl isocyanate, the reaction may be represented by the following scheme:

In a preferred embodiment of methods a, b and c according to the invention, a 2,1,3-benzothiadiazin-(4)-one-2,2-dioxide or a salt thereof is reacted with a halogen compound, an alkyl sulfate or a sulfone ester in the presence or absence of an inert solvent and of an acid binder at a temperature of from $-30°$ to $+150°$ C., preferably from $+10°$ to $+90°$ C., for from 10 minutes to 6 hours, at atmospheric or superatmospheric pressure, and continuously or batchwise.

In method d according to the invention, for instance a compound of the formula V is reacted with a salt of O-alkyl-N-alkylaminothiophosphoric acid, hydrocyanic acid, thiocyanic acid, hydrazoic acid, ethoxydithiocarbamic acid or of an unsubstituted or substituted carbamic or thiocarbamic acid, or with an O,O,O-trialkylphosphite or thiourea, in the presence or absence of a solvent and of an acid binder at a temperature of from $-30°$ to $+150°$ C., preferably from $+10°$ to $+90°$ C., for from 10 minutes to 6 hours, at atmospheric or superatmospheric pressure, and continuously or batchwise.

In method e according to the invention, for instance a compound of the formula VI is reacted with an isocyanate of the formula VII in the presence or absence of a solvent at a temperature of from $-30°$ to $+150°$ C., preferably from $+10°$ to $+90°$ C., for from 30 minutes to 6 hours, at atmospheric or superatmospheric pressure, and continuously or batchwise.

Preferred inert solvents in the processes according to the invention include hydrocarbons such as ligroin, benzene fractions, e.g., those within a boiling range of from 70° to 140° C., cyclohexane, pentane, hexane, petroleum ether, and o-, m- and p-xylene; nitrohydrocarbons such as nitrobenzene and nitroethane; nitriles such as acetonitrile, butyronitrile and isobutyronitrile; ethers such as diethyl ether, di-n-propyl ether, tetrahydrofuran, dioxane and anisole; esters such as acetoacetic ester, ethyl acetate, isobutyl acetate, methyl benzoate and phenyl acetate; amides such as formamide, methylformamide and dimethylformamide; and ketones such as acetone, methyl ethyl ketone, cyclohexanone and acetophenone. If the compounds of the formula I or VI (and not their salts) are used, halohydrocarbons such as methylene chloride, chloroform, carbon tetrachloride, 1,1- and 1,2-dichloroethane, 1,1,1- and 1,1,2-trichloroethane, chlorobenzene, o-, m- and p-dichlorobenzene and o-, m- and p-chlorotoluene are also preferred solvents. If the salts of compounds of the formula I are used, water is also a preferred solvent in methods a, b and c. As acid binder, any of the agents conventionally used for this purpose may be employed. Preferred examples are alkali metal hydroxides, alkali metal carbonates and tertiary organic bases. Particularly suitable compounds are sodium hydroxide, sodium carbonate, sodium bicarbonate, triethylamine, pyridine, trimethylamine, α-, β- and γ-picoline, lutidine, N,N-dimethylaniline, N,N-dimethylcyclohexylamine, quinoline, tri-n-propylamine, n-propyldiisopropylamine and tri-n-butylamine.

In addition to starting materials I, their alkali metal, alkaline earth metal or ammonium salts may also be advantageously used as starting materials. The compounds of the formulae I, V and VI used as starting materials are advantageously employed in an amount of from 0.3 to 1, preferably 0.8 to 1, mole per mole of starting material II, III, IV or VII.

The starting materials may be added in any order. The following procedure is particularly preferred. A solution of starting materials II, III or IV in one of the abovementioned inert solvents is run into a solution or suspension of starting material I, or salt thereof, in one of the abovementioned inert solvents; alternatively, a solution or a suspension of a salt of O-alkyl-N-alkylaminothiophosphoric, hydrocyanic, thiocyanic, hydrazoic, alkoxydithiocarbamic or a substituted or unsubstituted carbamic or thiocarbamic acid, or of an O,O,O-trialkylphosphite or of thiourea in one of the abovementioned inert solvents is run into a solution of starting material V; alternatively, a solution of starting material VII in one of the abovementioned solvents is run into a solution of starting material VI. The reaction is then carried out in the abovementioned temperature range.

To accelerate the reaction of starting materials I with fluorine or chlorine compounds of the formula II, an alkali metal or alkaline earth metal salt of a heavy halogen atom, e.g., sodium or calcium iodide, may be added as catalyst. If a two-phase solvent system is used, quaternary ammonium compounds are also suitable as catalyst. The amount of catalysts to be used in accordance with the invention is from 0.1 to 10 wt%, based on starting material II. To isolate the compounds of the formula VIII from the reaction mixture in methods a to e of the invention, the reaction mixture is stirred—when solvents miscible with water are used—into a dilute aqueous alkaline solution. The oil which separates out is if desired extracted, washed with water and dried. If the solvent is only slightly polar and immiscible with water, the reaction solution may also be extracted direct with a dilute aqueous alkaline solution and water. If desired, the reaction mixture may also be preconcentrated, taken up in a solvent immiscible with water, and purified as described above. The desired end products are obtained by drying and concentrating the organic phase. If desired, they may be further purified in conventional manner, e.g., by recrystallization or chromatography.

EXAMPLE 1

At 22° C. and while stirring, 22.8 parts of methyl chloroacetate was introduced over a period of 10 minutes into a solution of 52.4 parts of 3-isopropyl-2,1,3-benzothiadiazin-(4)-one-2,2-dioxide-1-sodium salt in 200 parts of acetone. After stirring for 1 hour at 50° C., the reaction mixture was concentrated in vacuo, taken up in 250 parts of methylene chloride and extracted 3 times with 100 ml of 0.5 N caustic soda solution and with water. After drying over magnesium sulfate and concentration in vacuo, 1-methylcarbomethoxy-3-isopropyl-2,1,3-benzothiadiazin-(4)-one-2,2-dioxide was obtained in the form of colorless crystals; m.p.: 93°–96° C.

EXAMPLE 2

While stirring and at 24° C., 25.3 parts of 1-chlorobutyne-3 was dripped over a period of 10 minutes into a solution of 1 part of sodium iodide and 80 parts of 3-isopropyl-2,1,3-benzothiadiazin-(4)-one-2,2-dioxide-1-potassium salt in 630 parts of acetonitrile. After the reaction mixture had been stirred for 10 hours at 82° C., it was concentrated in vacuo, taken up in 300 parts of methylene chloride, extracted four times with 0.5 N caustic soda solution, each time with 100 ml, and extracted with water. After drying over magnesium sulfate, chormatographing using neutral aluminum oxide and concentration in vacuo, 1-butyn-(3')-yl-3-isopropyl-2,1,3-benzothiadiazin-(4)-one-2,2-dioxide was isolated in the form of colorless crystals; m.p.: 66°–70° C.

EXAMPLE 3

At 10° C. and while stirring, 16.5 parts of diethyl sulfate was introduced over a period of 15 minutes into a solution of 24 parts of 3-isopropyl-2,1,3-benzothiadiazin-(4)-one-2,2-dioxide and 4.5 parts of sodium hydroxide in 25 parts of water. The reaction mixture was then stirred for 10 hours at 20° C., 150 parts of 1,2-dichloroethane was added, and the resultant mixture was extracted twice with 0.5 N caustic soda solution, each time in an amount of 70 ml, and with water. After drying, concentration in vacuo and trituration with cyclohexane, 1-ethyl-3-isopropyl-2,1,3-benzothiadiazin-(4)-one-2,2-dioxide was isolated in the form of colorless crystals; m.p.: 56°–58° C.

EXAMPLE 4

At 10° C. and while stirring, a solution of 16 parts of the dimethylammonium salt of O-ethyl-N-isopropylaminothiophosphoric acid in 60 parts of acetonitrile was introduced over a period of 10 minutes into a solution of 20.2 parts of 1-chloromethyl-3-isopropyl-2,1,3-benzothiadiazin-(4)-one-2,2-dioxide in 160 parts of acetonitrile. The reaction mixture was then stirred for 2 hours at 25° C., concentrated in vacuo, taken up in 200 parts of diethyl ether, and extracted 3 times with a 10% sodium bicarbonate solution, each time with 100 parts, and with water. After drying over magnesium sulfate, concentration in vacuo and trituration with cyclohexane, 1-methyl(O-ethyl-N-isopropylaminophosphorothio)-3-isopropyl-2,1,3-benzothiadiazin-(4)-one-2,2-dioxide was obtained in the form of colorless crystals; m.p.: 79°–84° C.

EXAMPLE 5

100 parts of 1-chloromethyl-3-isopropyl-2,1,3-benzothiadiazin-(4)-one-2,2-dioxide and 150 parts of sodium azide were stirred in 800 parts of dimethylformamide for 6 hours at 25° C. The suspension was then diluted with 5 times its volume of water. After 1 hour, the precipitated crystals were suction filtered and dried. There was obtained 100 parts (98% of theory) of 1-azidomethyl-3-isopropyl-2,1,3-benzothiadiazin-(4)-one-2,2-dioxide; m.p.: 83° C.

Further active ingredients corresponding to the general formula were prepared by analogous methods. They are listed in Table I, m denoting O.

TABLE 1

| R¹ | R² | Y | n | m.p. (°C.) |
|---|---|---|---|---|
| $C_2H_5$ | $CH_3$ | O | 2 | |
| n-$C_3H_7$ | $CH_3$ | O | 2 | 39 |
| i-$C_3H_7$ | $CH_3$ | O | 2 | |
| ◁ | $CH_3$ | O | 2 | |
| n-$C_4H_9$ | $CH_3$ | O | 2 | |
| $CH_3$ | $CH_3$ | S | 2 | |
| $CH_3$ | $CH_3$ | O | 1 | |
| i-$C_3H_7$ | $CH_3$ | O | 1 | |
| i-$C_3H_7$ | $CH_3$ | S | 1 | |
| i-$C_4H_9$ | $CH_3$ | O | 2 | |
| sec-$C_4H_9$ | $CH_3$ | O | 2 | |
| tert-$C_4H_9$ | $CH_3$ | O | 2 | |
| $CH_3$ | $C_2H_5$ | O | 2 | |
| $C_2H_5$ | $C_2H_5$ | O | 2 | |
| $C_2H_5$ | $C_2H_5$ | O | 1 | |
| n-$C_3H_7$ | $C_2H_5$ | O | 2 | |
| n-$C_3H_7$ | $C_2H_5$ | S | 2 | |
| i-$C_3H_7$ | $C_2H_5$ | O | 2 | |
| ◁ | $C_2H_5$ | O | 2 | |
| n-$C_3H_7$ | $C_2H_5$ | O | 2 | |
| sec-$C_4H_9$ | $C_2H_5$ | O | 2 | |
| i-$C_4H_9$ | $C_2H_5$ | O | 2 | |
| tert-$C_4H_9$ | $C_2H_5$ | O | 2 | |
| i-$C_3H_7$ | $C_2H_5$ | S | 2 | |
| $CH_3$ | n-$C_3H_7$ | O | 2 | |
| $C_2H_5$ | n-$C_3H_7$ | O | 2 | |
| i-$C_3H_7$ | n-$C_3H_7$ | O | 2 | |
| n-$C_3H_7$ | n-$C_3H_7$ | O | 2 | |
| i-$C_3H_7$ | n-$C_3H_7$ | O | 1 | |
| n-$C_4H_9$ | n-$C_3H_7$ | O | 2 | |
| i-$C_4H_9$ | n-$C_3H_7$ | O | 2 | |
| sec-$C_4H_9$ | n-$C_3H_7$ | O | 2 | |
| tert-$C_4H_9$ | n-$C_3H_7$ | O | 2 | |
| $C_2H_5$ | n-$C_3H_7$ | S | 2 | |
| ◁ | n-$C_3H_7$ | O | 2 | |
| ⬡-H | n-$C_3H_7$ | O | 2 | |
| $C_{10}H_{21}$ | n-$C_3H_7$ | O | 2 | |
| $C_9H_{19}$ | n-$C_3H_7$ | O | 2 | |
| n-$C_5H_{11}$ | n-$C_3H_7$ | O | 2 | |
| sec-$C_4H_9$ | n-$C_3H_7$ | O | 1 | |
| $CH_3$ | i-$C_3H_7$ | O | 2 | 54–55 |
| n-$C_3H_7$ | i-$C_3H_7$ | O | 2 | $n_D^{25} = 1.5359$ |
| i-$C_3H_7$ | i-$C_3H_7$ | O | 2 | 44–45 |
| ◁ | i-$C_3H_7$ | O | 2 | |
| $CH_3$ | i-$C_3H_7$ | S | 2 | |
| $CH_3$ | i-$C_3H_7$ | O | 1 | |
| n-$C_4H_9$ | i-$C_3H_7$ | O | 2 | |
| i-$C_4H_9$ | i-$C_3H_7$ | O | 2 | |
| sec-$C_4H_9$ | i-$C_3H_7$ | O | 2 | $n_D^{25} = 1.5316$ |
| sec-$C_4H_9$ | i-$C_3H_7$ | O | 1 | |
| $C_2H_5$ | i-$C_3H_7$ | S | 2 | |
| tert-$C_4H_9$ | i-$C_3H_7$ | O | 2 | |
| n-$C_5H_{11}$ | i-$C_3H_7$ | O | 2 | |
| —CH(n-$C_3H_7$)($CH_3$) | i-$C_3H_7$ | O | 2 | |
| —CH(CH($CH_3$)$_2$)($CH_3$) | i-$C_3H_7$ | O | 2 | |
| —CH($C_2H_5$)$_2$ | i-$C_3H_7$ | O | 2 | |
| —CH($C_2H_5$)$_2$ | i-$C_3H_7$ | O | 1 | |
| —$CH_2$C($CH_3$)$_3$ | i-$C_3H_7$ | O | 2 | |
| —$CH_2$—$CH_2$—CH($CH_3$)$_2$ | i-$C_3H_7$ | O | 2 | $n_D^{25} = 1.5278$ |
| —C($CH_3$)$_2$$C_2H_5$ | i-$C_3H_7$ | O | 2 | |
| —$CH_2$—CH($CH_3$)—$C_2H_5$ | i-$C_3H_7$ | O | 2 | |

TABLE 1-continued

| | | | | |
|---|---|---|---|---|
|  | i-C₃H₇ | O | 2 | |
| -n-C₆H₁₃ | i-C₃H₇ | O | 2 | |
|  | i-C₃H₇ | O | 2 | |
| n-C₃H₇ | i-C₃H₇ | O | 1 | |
| n-C₅H₁₁ | i-C₃H₇ | O | 2 | |
| n-C₇H₁₅ | i-C₃H₇ | O | 2 | |
| n-C₈H₁₇ | i-C₃H₇ | O | 2 | |
| n-C₉H₁₉ | i-C₃H₇ | O | 2 | |
| n-C₁₀H₂₁ | i-C₃H₇ | O | 2 | |
| $CH_2-\overset{O}{\underset{\|}{S}}-CH_3$ | i-C₃H₇ | O | 2 | $n_D^{25} = 1.5561$ |
| $CH_2-\overset{O}{\underset{\|}{S}}-C_2H_5$ | i-C₃H₇ | O | 2 | $n_D^{25} = 1.5610$ |
| CH₃ | n-C₄H₉ | O | 2 | |
| C₂H₅ | n-C₄H₉ | O | 2 | |
| n-C₃H₇ | n-C₄H₉ | O | 2 | |
| n-C₃H₇ | n-C₄H₉ | S | 2 | |
| i-C₃H₇ | n-C₄H₉ | O | 2 | |
| n-C₄H₉ | n-C₄H₉ | O | 2 | |
| i-C₄H₉ | n-C₄H₉ | O | 2 | |
| tert-C₄H₉ | n-C₄H₉ | O | 2 | |
| 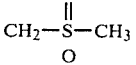 | n-C₄H₉ | O | 2 | |
| CH₃ | sec-C₄H₉ | O | 2 | |
| C₂H₅ | sec-C₄H₉ | O | 2 | 68–71 |
| n-C₃H₇ | sec-C₄H₉ | O | 2 | |
| i-C₃H₇ | sec-C₄H₉ | O | 2 | |
| tert-C₄H₉ | sec-C₄H₉ | O | 2 | |
| CH₃ | i-C₄H₉ | O | 2 | |
| C₂H₅ | i-C₄H₉ | O | 2 | |
| n-C₃H₇ | i-C₄H₉ | O | 1 | |
| i-C₃H₇ | i-C₄H₉ | O | 2 | |
| n-C₄H₉ | i-C₄H₉ | S | 2 | |
| CH₃ | tert-C₄H₉ | O | 2 | |
| C₂H₅ | tert-C₄H₉ | O | 2 | |
| n-C₃H₇ | tert-C₄H₉ | O | 2 | |
| n-C₄H₉ | tert-C₄H₉ | O | 1 | |
| CH₃ | 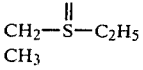 | O | 2 | |
| C₂H₅ |  | O | 2 | |
| tert-C₄H₉ |  | O | 2 | |
| CH₃ | —CH(C₂H₅)₂ | O | 2 | |
| C₂H₅ | —CH(C₂H₅)₂ | O | 2 | |
| n-C₃H₇ | —CH(C₂H₅)₂ | O | 2 | |
| i-C₃H₇ | —CH(C₂H₅)₂ | O | 2 | |
| tert-C₄H₉ | —CH(C₂H₅)₂ | O | 2 | |
| $CH_2-\overset{O}{\underset{\underset{O}{\|}}{S}}-CH_3$ | i-C₃H₇ | O | 2 | 111–115 |
| $CH_2-\overset{O}{\underset{\underset{O}{\|}}{S}}-C_2H_5$ | i-C₃H₇ | O | 2 | 98–100 |
| CH₃ |  | O | 2 | |
| C₂H₅ | 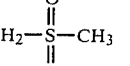 | O | 2 | |
| n-C₃H₇ | 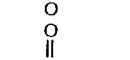 | O | 2 | |
| tert-C₄H₉ |  | O | 2 | |
| CH₃ |  | O | 2 | |

TABLE 1-continued

| | | | | |
|---|---|---|---|---|
| $C_2H_5$ | —⟨H⟩ (cyclohexyl) | O | 2 | |
| n-$C_3H_7$ | —⟨H⟩ (cyclohexyl) | O | 2 | |
| n-$C_3H_7$ | —CH(CH$_3$)CH(CH$_3$)$_2$ | O | 2 | 68–73 |
| n-$C_3H_7$ | —CH(C$_2$H$_5$)(CH$_2$)$_3$CH$_3$ | O | 2 | |
| $CH_3$ | —CH$_2$—CH$_2$Cl | O | 2 | |
| n-$C_3H_7$ | —CH$_2$—CH$_2$Cl | O | 2 | |
| i-$C_3H_7$ | —CH$_2$—CH$_2$Cl | O | 2 | |
| i-$C_3H_7$ | —CH$_2$—CH$_2$Cl | O | 1 | |
| $CH_3$ | —CH(CH$_3$)CH$_2$F | O | 2 | |
| $C_2H_5$ | —CH(CH$_3$)CH$_2$F | O | 2 | |
| $CH_3$ | —CH(CH$_2$F)$_2$ | O | 2 | |
| n-$C_3H_7$ | —CH(CH$_2$F)$_2$ | O | 2 | |
| $C_2H_5$ | —CH(CH$_2$F)$_2$ | S | 2 | |
| —CH=CH$_2$ | CH$_3$ | O | 2 | |
| —C≡C—H | CH$_3$ | O | 2 | |
| —CH=CH—CH$_3$ | CH$_3$ | O | 2 | |
| —C≡C—CH$_3$ | CH$_3$ | O | 2 | |
| —CH$_2$—CH=CH$_2$ | CH$_3$ | O | 2 | |
| —CH$_2$—C≡CH | CH$_3$ | O | 2 | 122–126 |
| —CH$_2$—CH=CH—CH$_3$ | CH$_3$ | O | 2 | |
| —CH$_2$—C≡C—CH$_3$ | CH$_3$ | O | 2 | |
| —CH$_2$—C(CH$_3$)=CH$_2$ | CH$_3$ | O | 2 | |
| —CH(CH$_3$)CH=CH$_2$ | CH$_3$ | O | 2 | |
| —CH(CH$_3$)C≡CH | CH$_3$ | O | 2 | |
| —CH$_2$—CH$_2$—CH=CH$_2$ | CH$_3$ | O | 2 | |
| —CH$_2$—CH$_2$—C≡CH | CH$_3$ | O | 2 | |
| —CH(CH$_3$)C(CH$_3$)=CH$_2$ | CH$_3$ | O | 2 | |
| —CH$_2$—C(CH$_3$)=CH—CH$_3$ | CH$_3$ | O | 2 | |
| —CH$_2$—CH=C(CH$_3$)$_2$ | CH$_3$ | O | 2 | |

TABLE 1-continued

| R1 | R2 | X | n | |
|---|---|---|---|---|
| -C(CH3)2-CH=CH2 | CH3 | O | 2 | |
| -C(CH3)2-C≡CH | CH3 | O | 2 | |
| -C(CH3)2-C≡CH | CH3 | S | 2 | |
| -CH2-CH2-C(CH3)=CH2 | CH3 | O | 2 | |
| -CH2-C≡CH | CH3 | O | 1 | |
| -CH2-C≡CH | CH3 | S | 2 | |
| -CH=CH2 | C2H5 | O | 2 | |
| -C≡CH | C2H5 | O | 2 | |
| -CH=CH-CH3 | C2H5 | O | 2 | |
| -C≡C-CH3 | C2H5 | O | 2 | |
| -CH2-CH=CH2 | C2H5 | O | 2 | |
| -CH2-C≡CH | C2H5 | O | 2 | 71-75 |
| -CH2-CH=CH-CH3 | C2H5 | O | 2 | |
| -CH2-C≡C-CH3 | C2H5 | O | 2 | |
| -CH2-C(CH3)=CH2 | C2H5 | O | 2 | |
| -CH(CH3)-CH=CH2 | C2H5 | O | 2 | |
| -CH(CH3)-C≡CH | C2H5 | O | 2 | |
| -CH2-CH2-CH=CH2 | C2H5 | O | 2 | |
| -CH2-CH2-C≡CH | C2H5 | O | 2 | |
| -CH(CH3)-C(CH3)=CH2 | C2H5 | O | 2 | |
| -CH2-C(CH3)=CH-CH3 | C2H5 | O | 2 | |
| -CH2CH=C(CH3)2 | C2H5 | O | 2 | |
| -C(CH3)2-CH=CH2 | C2H5 | O | 2 | |
| -C(CH3)2-C≡CH | C2H5 | O | 2 | |
| -CH=CH2 | n-C3H7 | O | 2 | |
| -C≡CH | n-C3H7 | O | 2 | |
| -CH=CH-CH3 | n-C3H7 | O | 2 | |
| -C≡CH-CH3 | n-C3H7 | O | 2 | |
| -CH2-CH=CH2 | n-C3H7 | O | 2 | |
| -CH2-C≡CH | n-C3H7 | O | 2 | 53-57 |
| -CH2-CH=CH-CH3 | n-C3H7 | O | 2 | |
| -CH2-C≡C-CH3 | n-C3H7 | O | 2 | |
| -CH2-C(CH3)=CH2 | n-C3H7 | O | 2 | |

TABLE 1-continued

| | | | | |
|---|---|---|---|---|
| −CH(CH=CH₂)CH₃ | n-C₃H₇ | O | 2 | |
| −CH(C≡CH)CH₃ | n-C₃H₇ | O | 2 | |
| −CH₂−CH₂−CH=CH₂ | n-C₃H₇ | O | 2 | |
| −CH₂−CH₂−C≡CH | n-C₃H₇ | O | 2 | |
| −CH(CH₃)C(=CH₂)CH₃ | n-C₃H₇ | O | 2 | |
| −CH₂−C(CH₃)=CH−CH₃ | n-C₃H₇ | O | 2 | |
| −CH₂−CH=C(CH₃)₂ | n-C₃H₇ | O | 2 | |
| −C(CH₃)₂−CH=CH₂ | n-C₃H₇ | O | 2 | |
| −C(CH₃)₂−C≡CH | n-C₃H₇ | O | 2 | |
| −CH₂−C≡CH | n-C₃H₇ | O | 1 | |
| −CH₂−C≡CH | n-C₃H₇ | S | 2 | |
| −CH=CH₂ | i-C₃H₇ | O | 2 | |
| −C≡CH | i-C₃H₇ | O | 2 | |
| −CH=CH−CH₃ | i-C₃H₇ | O | 2 | |
| −C≡C−CH₃ | i-C₃H₇ | O | 2 | |
| −CH₂−CH=CH₂ | i-C₃H₇ | O | 2 | 41–43 |
| −CH₂−C≡CH | i-C₃H₇ | O | 2 | 108–112 |
| −CH₂−CH=CH−CH₃ | i-C₃H₇ | O | 2 | $n_D^{25} = 1.5436$ |
| −CH₂−C≡C−CH₃ | i-C₃H₇ | O | 2 | |
| −CH₂−C(CH₃)=CH₂ | i-C₃H₇ | O | 2 | |
| −CH(CH=CH₂)CH₃ | i-C₃H₇ | O | 2 | |
| −CH(C≡CH)CH₃ | i-C₃H₇ | O | 2 | |
| −CH₂−CH₂−CH=CH₂ | i-C₃H₇ | O | 2 | |
| −CH₂−CH₂−C≡CH | i-C₃H₇ | O | 2 | 66–69 |
| −CH(CH₃)C(=CH₂)CH₃ | i-C₃H₇ | O | 2 | |
| −CH₂−C(CH₃)=CH−CH₃ | i-C₃H₇ | O | 2 | |
| −CH₂−CH=C(CH₃)₂ | i-C₃H₇ | O | 2 | |
| −C(CH₃)₂−CH=CH₂ | i-C₃H₇ | O | 2 | |

TABLE 1-continued

| R | R' | X | n | mp |
|---|---|---|---|---|
| —CH₂—(3-methylisoxazol-5-yl) | i-C₃H₇ | O | 2 | 114–115 |
| —CH₂—(4-chloro-3-methylisoxazol-5-yl) | i-C₃H₇ | O | 2 | 106–109 |
| —C(CH₃)₂—C≡CH | i-C₃H₇ | O | 2 | |
| —CH₂—CH=CH₂ | i-C₃H₇ | S | 2 | |
| —CH₂—C≡CH | i-C₃H₇ | O | 1 | |
| —CH₂—P(O)(OCH₃)₂ | i-C₃H₇ | O | 2 | 71–73 |
| —CH₂—P(O)(OC₂H₅)₂ | i-C₃H₇ | O | 2 | 75–77 |
| —CH₂—CH=CH₂ | cyclopropyl | O | 2 | |
| —CH₂—C≡CH | cyclopropyl | O | 2 | |
| —CH₂—C≡CH | cyclopentyl | O | 2 | |
| —CH₂—CH=CH₂ | n-C₄H₉ | O | 2 | |
| —CH₂—C≡CH | n-C₄H₉ | O | 2 | |
| —CH₂—CH=CH—CH₃ | n-C₄H₉ | O | 2 | |
| —CH₂—C≡C—CH₃ | n-C₄H₉ | O | 2 | |
| —CH(CH₃)—CH=CH₂ | n-C₄H₉ | O | 2 | |
| —CH(CH₃)—C≡CH | n-C₄H₉ | O | 2 | |
| —CH=CH₂ | sec-C₄H₉ | O | 2 | |
| —C≡CH | sec-C₄H₉ | O | 2 | |
| —CH=CH—CH₃ | sec-C₄H₉ | O | 2 | |
| —C≡C—CH₃ | sec-C₄H₉ | O | 2 | |
| —CH₂—CH=CH₂ | sec-C₄H₉ | O | 2 | |
| —CH₂—C≡CH | sec-C₄H₉ | O | 2 | 55–59 |
| —CH₂—C≡CH | sec-C₄H₉ | S | 2 | |
| —CH₂—CH=CH—CH₃ | sec-C₄H₉ | O | 1 | |
| —CH₂—C≡C—CH₃ | sec-C₄H₉ | O | 2 | |
| —CH₂—C(CH₃)=CH₂ | sec-C₄H₉ | O | 2 | |
| —CH(CH₃)—CH=CH₂ | sec-C₄H₉ | O | 2 | |
| —CH(CH₃)—C≡CH | sec-C₄H₉ | O | 2 | |
| —CH₂—C≡CH | —CH(C₂H₅)₂ | O | 2 | |
| —CH₂—C≡CH | —CH(CH₃)CH(CH₃)₂ | O | 2 | |
| —CH₂—C≡CH | cyclopentyl | O | 2 | |
| —CH₂—C≡CH | cyclohexyl | O | 2 | |
| —CH₂—C≡CH | —CH₂—CH₂Cl | O | 2 | |

TABLE 1-continued

| | | | | |
|---|---|---|---|---|
| —CH$_2$—C≡CH | —CH(CH$_3$)CH$_2$F | O | 2 | |
| —CH$_2$—C≡CH | —CH(CH$_2$F)CH$_2$F | O | 2 | |
| —CH$_2$—C≡CH | C$_6$H$_5$ | O | 2 | |
| —CH$_2$—C≡CH | 3-F-C$_6$H$_4$ | S | 2 | |
| —CH$_2$—C≡CH | 3-CH$_3$-C$_6$H$_4$ | O | 2 | |
| —CH$_2$—CH$_2$Cl | C$_2$H$_5$ | O | 2 | |
| —CH$_2$—CH$_2$Br | i-C$_3$H$_7$ | O | 2 | $n_D^{25} = 1.5648$ |
| —CH$_2$—CH$_2$Cl | i-C$_3$H$_7$ | S | 2 | |
| —CH$_2$—C≡C—CH$_2$Cl | i-C$_3$H$_7$ | O | 2 | 68–72 |
| Cl$_3$C—CH(NHC(O)CH$_3$)— | i-C$_3$H$_7$ | O | 2 | 221 |
| Cl$_3$C—CH(NHCO$_2$C$_2$H$_5$)— | i-C$_3$H$_7$ | O | 2 | 170 |
| Cl$_3$C—CH(NHCH(O))— | i-C$_3$H$_7$ | O | 2 | 209–211 |
| —CH(CO$_2$CH$_3$)—S—CH$_2$—CO$_2$CH$_3$ | i-C$_3$H$_7$ | O | 2 | 89–90 |
| —CH$_2$—C≡C—CH$_2$Cl | sec-C$_4$H$_9$ | O | 2 | |
| —CH$_2$—CH=CH—CH$_2$Cl | i-C$_3$H$_7$ | O | 2 | |
| —CH$_2$CH$_2$—O—CH$_3$ | CH$_3$ | O | 2 | |
| —CH$_2$—CH$_2$—O—CH$_3$ | C$_2$H$_5$ | O | 2 | |
| —CH$_2$—CH$_2$—O—CH$_3$ | n-C$_3$H$_7$ | O | 2 | |
| —CH$_2$—CH$_2$—O—CH$_3$ | i-C$_3$H$_7$ | O | 2 | 62–63 |
| —CH$_2$—CH$_2$—O—CH$_3$ | i-C$_3$H$_7$ | O | 1 | |
| —CH$_2$—CH$_2$—O—i-C$_3$H$_7$ | i-C$_3$H$_7$ | O | 2 | |
| —CH$_2$—CH$_2$—O—CH$_3$ | n-C$_4$H$_9$ | O | 2 | |
| —CH$_2$—CH$_2$—O—CH$_3$ | sec-C$_4$H$_9$ | O | 2 | |
| —CH$_2$—CH$_2$—S—CH$_3$ | CH$_3$ | O | 2 | |
| —CH$_2$—CH$_2$—S—CH$_3$ | n-C$_3$H$_7$ | O | 2 | |
| —CH$_2$—CH$_2$—S—CH$_3$ | i-C$_3$H$_7$ | O | 2 | |
| —CH$_2$—CH$_2$—S—CH$_3$ | n-C$_4$H$_9$ | O | 2 | |
| —CH$_2$—CH$_2$—S—CH$_3$ | sec-C$_4$H$_9$ | O | 2 | |
| —CH$_2$—CO$_2$CH$_3$ | CH$_3$ | O | 2 | |
| —CH$_2$—CO$_2$CH$_3$ | C$_2$H$_5$ | O | 2 | |
| —CH$_2$CO$_2$CH$_3$ | n-C$_3$H$_7$ | O | 2 | |
| —CH$_2$CO$_2$CH$_3$ | i-C$_3$H$_7$ | S | 2 | |
| —CH$_2$CO$_2$H | i-C$_3$H$_7$ | O | 2 | 98 |
| —CH$_2$—CO$_2$CH$_3$ | n-C$_4$H$_9$ | O | 2 | |
| —CH$_2$—CO$_2$CH$_3$ | sec-C$_4$H$_9$ | O | 2 | |
| —CH$_2$—CO$_2$CH$_3$ | tert-C$_4$H$_9$ | O | 2 | |
| —CH$_2$—CH$_2$CO$_2$CH$_3$ | i-C$_3$H$_7$ | O | 2 | |
| —CH(CO$_2$CH$_3$)CH$_3$ | i-C$_3$H$_7$ | O | 2 | |
| —CH$_2$—CH=CH—CO$_2$CH$_3$ | i-C$_3$H$_7$ | O | 2 | |
| —CH$_2$CH$_2$OH | i-C$_3$H$_7$ | O | 2 | $n_D^{25} = 1.5459$ |
| —CH$_2$CH$_2$—S—C$_6$H$_5$ | i-C$_3$H$_7$ | O | 2 | $n_D^{25} = 1.5929$ |
| —CH$_2$—C(O)—CH$_3$ | C$_2$H$_5$ | O | 2 | |
| —CH$_2$—C(O)—CH$_3$ | n-C$_3$H$_7$ | O | 2 | |

TABLE 1-continued

| | | | | |
|---|---|---|---|---|
| −CH₂−C(=O)−CH₃ | i-C₃H₇ | O | 2 | $n_D^{25} = 1.5464$ |
| −CH₂−C(=O)−CH₃ | sec-C₄H₉ | O | 2 | |
| −CH₂−C₆H₅ | n-C₂H₅ | O | 2 | |
| −CH₂−C₆H₅ | i-C₃H₇ | O | 2 | 82−86 |
| −CH₂−C≡CH | −CH(CH=CH₃)(CH₃) | O | 2 | |
| −CH₂−CH₂−C(=O)−CH₃ | i-C₃H₇ | O | 2 | 69−73 |
| −CH(C≡CH)(CH₃) | −CH(C≡CH)(CH₃) | O | 2 | |
| −CH₂−C≡CH | −CH₂−C≡CH | O | 2 | |
| −CH₂−C≡CH | −CH₂−C≡CH | S | 2 | |
| −CH₂−C(=O)−NH₂ | CH₃ | O | 2 | |
| −CH₂−C(=O)−NH₂ | i-C₃H₇ | O | 2 | 161−163 |
| −CH₂−C(=O)−NHCH₃ | C₂H₅ | O | 2 | |
| −CH₂−C(=O)−NHCH₃ | i-C₃H₇ | O | 2 | 136−137 |
| −CH₂−C(=O)−NHCH₃ | sec-C₄H₉ | O | 2 | |
| −CH₂−C(=O)−N(CH₃)₂ | i-C₃H₇ | O | 2 | 132−133 |
| −CH₂−C(=S)−NH₂ | i-C₃H₇ | O | 2 | 106 |
| −CH₂−C(=O)−N(CH₃)₂ | n-C₃H₇ | O | 2 | |
| −CH₂−SCN | i-C₃H₇ | O | 2 | 124−126 |
| −CH₂−SCN | C₂H₅ | O | 2 | |
| −CH₂−CN | n-C₃H₇ | O | 2 | |
| −CH₂−CN | i-C₃H₇ | O | 2 | 119−121 |
| −CH₂−CN | i-C₃H₇ | S | 2 | |
| −CH₂−CN | i-C₃H₇ | O | 1 | |
| −CH₂−CH₂CN | n-C₃H₇ | O | 2 | |
| −CH₂−CH₂CN | i-C₃H₇ | O | 2 | 115−117 |
| −CH₂−CH₂−C(=O)−NH₂ | C₂H₅ | O | 2 | |
| −CH₂−CH₂−C(=O)−NH₂ | n-C₃H₇ | O | 2 | |
| −CH₂−CH₂−C(=O)−NH₂ | i-C₃H₇ | O | 2 | 139−141 |
| −CH₂−N(phthalimido) | i-C₃H₇ | O | 2 | 216−217 |
| −CH₂−N(phthalimido) | n-C₃H₇ | O | 2 | |

TABLE 1-continued
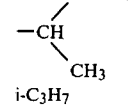

| | | | | |
|---|---|---|---|---|
| 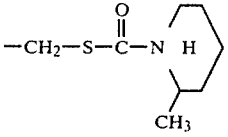 | i-C$_3$H$_7$ | O | 2 | 107 |
| 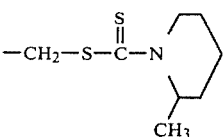 | sec-C$_4$H$_9$ | O | 2 | |
| 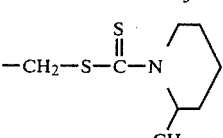 | i-C$_3$H$_7$ | O | 2 | 110–113 |
| 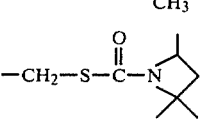 | i-C$_3$H$_7$ | O | 2 | 73–76 |
| 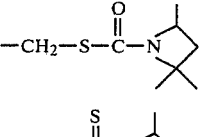 | sec-C$_4$H$_9$ | O | 2 | |
| 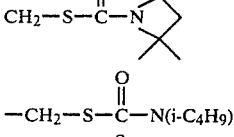 | i-C$_3$H$_7$ | O | 2 | 72–74 |
| —CH$_2$—S—C(=O)—N(i-C$_4$H$_9$)$_2$ | i-C$_3$H$_7$ | O | 2 | 101–102 |
| 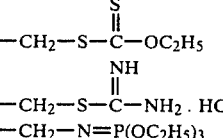 | i-C$_3$H$_7$ | O | 2 | 91–92 |
| 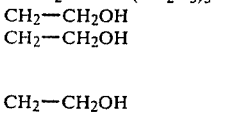 | i-C$_3$H$_7$ | O | 2 | 181 |
| —CH$_2$—N=P(OC$_2$H$_5$)$_3$ | i-C$_3$H$_7$ | O | 2 | n$_D^{25}$ = 1.5072 |
| CH$_2$—CH$_2$OH | sec-C$_4$H$_9$ | O | 2 | |
| CH$_2$—CH$_2$OH | 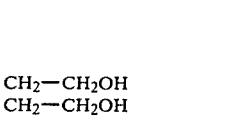 | O | 2 | |
| CH$_2$—CH$_2$OH | 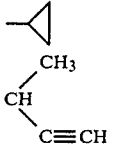 | O | 2 | |
| CH$_2$—CH$_2$OH | C$_6$H$_5$ | O | 2 | |
| CH$_2$—CH$_2$OH | 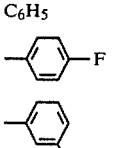 | O | 2 | |
| CH$_2$—CH$_2$OH | 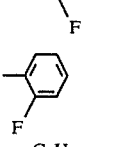 | O | 2 | |
| CH$_2$—CH$_2$OH | 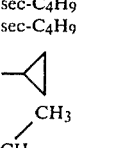 | O | 2 | |
| CH$_2$SCN | sec-C$_4$H$_9$ | O | 1 | |
| CH$_2$CN | sec-C$_4$H$_9$ | O | 2 | |
| CH$_2$SCN | 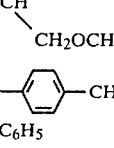 | O | 2 | |
| CH$_2$SCN |  | O | 2 | |
| CH$_2$SCN |  | O | 2 | |
| CH$_2$CO$_2$CH$_3$ | C$_6$H$_5$ | O | 2 | |

TABLE 1-continued

| X | Ring position | m | R¹ | R² | Y | n | m.p. (°C.) |
|---|---|---|---|---|---|---|---|
| $CH_2CO_2CH_3$ | | | ![meta-tolyl] | | O | 2 | |
| $CH_2CO_2CH_3$ | | | ![2,3-dimethylphenyl] | | S | 2 | |
| $(CH_2)_4OH$ | | | $i$-$C_3H_7$ | | O | 2 | |
| $CH_3$ | 5,6,7 | 1 | $CH_3$ | $i$-$C_3H_7$ | O | 2 | |
| $CH_3$ | 8 | 1 | $CH_2$—C≡CH | $i$-$C_3H_7$ | O | 2 | 140–144 |
| $CH_3$ | 8 | 1 | $CH_2$—C≡CH | $i$-$C_3H_7$ | S | 2 | |
| $CH_3$ | 8 | 1 | $CH_2CN$ | $i$-$C_3H_7$ | O | 2 | |
| $CH_3$ | 7 | 1 | $CH_2CN$ | $i$-$C_3H_7$ | O | 2 | |
| $CH_3$ | 5,6 | 1 | $CH_2CN$ | $i$-$C_3H_7$ | O | 2 | |
| $CH_3$ | 5,6,7,8 | 1 | $CH_2$—C≡C—$CH_2Cl$ | $i$-$C_3H_7$ | O | 2 | |
| $CH_3$ | 5,6,7,8 | 1 | tert-$C_4H_9$ | $i$-$C_3H_7$ | O | 2 | |
| $CH_3$ | 5,6,7,8 | 1 | tert-$C_4H_9$ | $i$-$C_3H_7$ | S | 2 | |
| $CH_3$ | 6,8 | 2 | $CH_2$—C≡CH | $i$-$C_3H_7$ | O | 2 | 98–101 |
| $CH_3$ | 6,8 | 2 | $CH_2CN$ | $i$-$C_3H_7$ | O | 2 | |
| $CH_3$ | 6,8 | 2 | $CH_2$—SCN | $i$-$C_3H_7$ | O | 2 | |
| $CH_3$ | 5,6,7,8 | 1 | $CH_2$—S—C(=O)—$N(CH_3)_2$ | $i$-$C_3H_7$ | O | 2 | |
| $CH_3$ | 5,6,7,8 | 1 | $CH_2$—S—C(=S)—$N(CH_3)_2$ | $i$-$C_3H_7$ | O | 2 | |
| $CH_3$ | 5,6,7,8 | 1 | $CH_2$—$CO_2CH_3$ | $i$-$C_3H_7$ | O | 2 | |
| $CH_3$ | 5,6,7,8 | 1 | $CH_2$—$CH_2$—C(=O)$NH_2$ | $i$-$C_3H_7$ | O | 2 | |
| $CH_3$ | 5,6,7,8 | 1 | $CH_2$—NHC(=O)—$CH_2Cl$ | $i$-$C_3H_7$ | O | 2 | |
| $CH_3$ | 5,6,7,8 | 1 | $CH_2$—C(=O)$N(CH_3)_2$ | $i$-$C_3H_7$ | O | 2 | |
| $CH_3$ | 5,6,7,8 | 1 | $CH_2$—O—C(=O)—NH—$C_6H_5$ | sec-$C_4H_9$ | O | 2 | |
| $CH_3$ | 5,6,7,8 | 1 | $CH_2N_3$ | $i$-$C_3H_7$ | O | 2 | |
| $CH_3$ | 5,6,7,8 | 1 | $CH_2$—$CH_2CN$ | $i$-$C_3H_7$ | O | 1 | |
| $CH_3$ | 8 | 1 | $CH_2$—$CH_2OH$ | $i$-$C_3H_7$ | O | 2 | 83–86 |
| Cl | 7 | 1 | $CH_2$—C≡CH | $i$-$C_3H_7$ | O | 2 | 97–103 |
| Cl | 7 | 1 | $CH_2N_3$ | $i$-$C_3H_7$ | O | 2 | |
| Cl | 5,6,7,8 | 1 | $CH_2CN$ | $i$-$C_3H_7$ | O | 2 | |
| Cl | 5,6,7,8 | 1 | tert-$C_4H_9$ | sec-$C_4H_9$ | O | 2 | |
| $CH_3$ | 5 | 1 | $CH_2$—C≡CH | $i$-$C_3H_7$ | O | 2 | 87–91 |
| Cl | 5,6,7,8 | 1 | $CH_2$—C≡C—$CH_2Cl$ | $CH_3$—CH(—C≡CH) | O | 2 | |
| I | 6 | 1 | $CH_2$—C≡CH | $i$-$C_3H_7$ | O | 2 | 105–109 |
| Cl | 8 | 1 | $CH_2SCN$ | $i$-$C_3H_7$ | O | 2 | |
| Cl | 5,6,7 | 1 | $CH_2SCN$ | $i$-$C_3H_7$ | O | 2 | |
| Cl | 5,6,7,8 | 1 | $CH_2CO_2CH_3$ | sec-$C_4H_9$ | O | 2 | |
| Cl | 5,6,7,8 | 1 | $CH_2$—C(=O)—$N(CH_3)_2$ | $CH_3$—CH(—$CH_2F$) | O | 2 | |
| Cl | 7 | 1 | $CH_2$—$CH_2OH$ | $i$-$C_3H_7$ | O | 2 | 93–96 |
| Cl | 5,6,8 | 1 | $CH_2$—$CH_2OH$ | $i$-$C_3H_7$ | O | 2 | |
| Cl | 7 | 1 | $CH_2$—C(=O)—$CH_3$ | $i$-$C_3H_7$ | O | 2 | 94–97 |
| F | 5,6,7,8 | 1 | $CH_2$—O—C(=O)—NH—$C_6H_4$—F | $i$-$C_3H_7$ | O | 2 | |
| F | 5,6,7,8 | 1 | $CH_2$—S—C(=S)$N(CH_3)_2$ | sec-$C_4H_9$ | S | 2 | |
| F | 5,6,7,8 | 1 | $CH_2$—S—C(=O)$N(CH_3)_2$ | $i$-$C_3H_7$ | O | 2 | |

TABLE 1-continued

| | | | | | | | |
|---|---|---|---|---|---|---|---|
| F | 5,6,7,8 | 1 | CH$_2$—S—P(=O)(OC$_2$H$_5$)(NHCH$_3$) | i-C$_3$H$_7$ | O | 2 | |
| C$_6$H$_5$ | 8 | 1 | CH$_2$CN | i-C$_3$H$_7$ | O | 2 | |
| C$_6$H$_5$ | 5,6,7,8 | 1 | CH$_2$SCN | sec-C$_4$H$_9$ | O | 2 | |
| C$_6$H$_5$ | 5,6,7,8 | 1 | CH$_2$CH$_2$OH | CH(CH$_3$)C≡CH | O | 2 | |
| Br | 6 | 1 | CH$_3$ | i-C$_3$H$_7$ | O | 1 | 135–137 |
| Br | 6 | 1 | CH$_2$C$_6$H$_5$ | i-C$_3$H$_7$ | O | 1 | 110–111 |
| C$_6$H$_5$ | 5,6,7,8 | 1 | CH$_2$N$_3$ | CH(CH$_3$)CH$_2$SCH$_3$ | O | 2 | |
| Cl | 8 | 1 | CH$_2$—C≡CH | i-C$_3$H$_7$ | O | 2 | 86–90 |
| SCN | 5,6,7,8 | 1 | CH$_2$N$_3$ | i-C$_3$H$_7$ | O | 2 | |
| SCN | 5,6,7,8 | 1 | CH$_2$CN | i-C$_3$H$_7$ | O | 2 | |
| SCN | 5,6,7,8 | 1 | CH$_2$CN | i-C$_3$H$_7$ | S | 2 | |
| SCN | 5,6,7,8 | 1 | CH$_2$CO$_2$CH$_3$ | i-C$_3$H$_7$ | S | 2 | |
| SCN | 5,6,7,8 | 1 | CH$_2$SCN | sec-C$_4$H$_9$ | O | 1 | |
| SCN | 5,6,7,8 | 1 | CH$_2$—S—C(=S)N(CH$_3$)$_2$ | i-C$_3$H$_7$ | O | 2 | |
| CO$_2$CH$_3$ | 5,6,7,8 | 1 | CH$_2$SCN | i-C$_3$H$_7$ | O | 2 | |
| CO$_2$CH$_3$ | 5,6,7,8 | 1 | CH$_2$CN | i-C$_3$H$_7$ | O | 2 | |
| CO$_2$CH$_3$ | 5,6,7,8 | 1 | CH$_2$—C≡CH | i-C$_3$H$_7$ | O | 2 | |
| CO$_2$CH$_3$ | 5,6,7,8 | 1 | CH$_2$—CH$_2$OH | i-C$_3$H$_7$ | O | 2 | |
| N(CH$_3$)$_2$ | 5,6,7,8 | 1 | CH$_2$N$_3$ | i-C$_3$H$_7$ | O | 2 | |
| N(CH$_3$)$_2$ | 5,6,7,8 | 1 | CH$_2$—C(=O)—N(CH$_3$)$_2$ | i-C$_3$H$_7$ | O | 2 | |
| N(CH$_3$)$_2$ | 5,6,7,8 | 1 | tert-C$_4$H$_9$ | sec-C$_4$H$_9$ | O | 2 | |
| OCH$_3$ | 5,6,7,8 | 1 | CH$_2$—C≡CH | i-C$_3$H$_7$ | O | 2 | |
| OCH$_3$ | 5,6,7,8 | 1 | CH$_2$SCN | i-C$_3$H$_7$ | O | 2 | |
| SCH$_3$ | 5,6,7,8 | 1 | CH$_2$CN | i-C$_3$H$_7$ | O | 2 | |
| SCH$_3$ | 5,6,7,8 | 1 | CH$_2$—C≡CH | CH(CH$_3$)CH$_2$F | O | 1 | |
| SCH$_3$ | 5,6,7,8 | 1 | CH$_2$—C≡C—CH$_2$Cl | i-C$_3$H$_7$ | O | 2 | |
| Cl | 6 | 1 | CH$_2$—C≡CH | i-C$_3$H$_7$ | O | 1 | 92–94 |
| Cl | 6 | 1 | CH$_2$C$_6$H$_5$ | C$_2$H$_5$ | O | 1 | 105–109 |
| SO$_2$CH$_3$ | 5,6,7,8 | 1 | CH$_2$N$_3$ | i-C$_3$H$_7$ | O | 2 | |
| SO$_2$CH$_3$ | 5,6,7,8 | 1 | CH$_2$—CH$_2$—C(=O)—NH$_2$ | i-C$_3$H$_7$ | O | 2 | |
| SO$_2$N(CH$_3$)$_2$ | 5,6,7,8 | 1 | CH$_2$—S—C(=O)N(CH$_3$)$_2$ | i-C$_3$H$_7$ | O | 2 | |
| SO$_2$N(CH$_3$)$_2$ | 5,6,7,8 | 1 | CH$_2$—CH$_2$OH | i-C$_3$H$_7$ | O | 2 | |
| CCl$_3$ | 5,6,7,8 | 1 | CH$_2$CN | i-C$_3$H$_7$ | O | 2 | |
| SO$_2$OCH$_3$ | 5,6,7,8 | 1 | CH$_2$CN | sec-C$_4$H$_9$ | O | 2 | |
| CCl$_3$ | 5,6,7,8 | 1 | CH$_2$—O—C(=O)NH—C$_6$H$_5$ | i-C$_3$H$_7$ | O | 2 | |
| CF$_3$ | 5,6,7,8 | 1 | CH$_2$N$_3$ | i-C$_3$H$_7$ | O | 2 | |
| CF$_3$ | 5,6,7,8 | 1 | CH$_2$—C≡CH | i-C$_3$H$_7$ | O | 2 | |
| CF$_3$ | 5,6,7,8 | 1 | CH$_2$CO$_2$CH$_3$ | sec-C$_4$H$_9$ | S | 2 | |
| C(=O)CH$_3$ | 5,6,7,8 | 1 | CH$_2$CN | i-C$_3$H$_7$ | O | 2 | |
| C(=O)CH$_3$ | 5,6,7,8 | 1 | CH$_2$SCN | i-C$_3$H$_7$ | O | 2 | |
| C(=O)H | 5,6,7,8 | 1 | CH$_2$CH$_2$CN | i-C$_3$H$_7$ | O | 2 | |
| OH | 5,6,7,8 | 1 | CH$_2$—C≡CH | i-C$_3$H$_7$ | O | 2 | |
| SH | 5,6,7,8 | 1 | CH$_2$—C≡CH | i-C$_3$H$_7$ | O | 2 | |
| SO$_2$NHCH$_3$ | 5,6,7,8 | 1 | CH$_2$—C(=O)—NHCH$_3$ | i-C$_3$H$_7$ | O | 2 | |
| OCF$_2$CH$_3$ | 5,6,7,8 | 1 | CH$_2$—C≡C—CH$_2$Cl | i-C$_3$H$_7$ | O | 1 | |
| OCF$_2$CF$_3$ | 5,6,7,8 | 1 | tert-C$_4$H$_9$ | i-C$_3$H$_7$ | O | 2 | |
| OCF$_2$CF$_3$ | 5,6,7,8 | 1 | CH$_2$—NH—C(=O)—CH$_2$Cl | i-C$_3$H$_7$ | O | 2 | |
| OCF$_2$CCl$_3$ | 5,6,7,8 | 1 | CH$_2$CN | i-C$_3$H$_7$ | O | 2 | |

TABLE 1-continued

| | | | | | | | |
|---|---|---|---|---|---|---|---|
| Cl | 6 | 1 | CH$_3$ | C$_2$H$_5$ | O | 1 | 96–98 |
| Br | 6 | 1 | CH$_3$ | C$_2$H$_5$ | O | 1 | 104–105 |
| NO$_2$ | 6 | 1 | CH$_2$SCN | ◁ | O | 2 | |
| NO$_2$ | 6 | 1 | CH$_2$N$_3$ | CH$_2$—CH=CH$_2$ | O | 2 | |
| NO$_2$ | 8 | 1 | CH$_2$CN | CH(CH$_3$)—C≡CH | O | 2 | |
| NO$_2$ | 5,7 | 1 | CH$_2$CO$_2$CH$_3$ | i-C$_3$H$_7$ | O | 2 | |
| NO$_2$, CH$_3$ | 6, 8 | 2 | CH$_2$N$_3$ | i-C$_3$H$_7$ | O | 2 | |
| NO$_2$ | 5,6,7,8 | 1 | CH$_2$—S—C(O)N(CH$_3$)$_2$ | i-C$_3$H$_7$ | O | 2 | |
| NO$_2$ | 5,6,7,8 | 1 | CH$_2$SCN | C$_6$H$_5$ | O | 2 | |
| NO$_2$ | 6 | 1 | CH$_2$SCN | —C$_6$H$_4$—F | O | 2 | |
| CH$_2$F | 5,6,7,8 | 1 | CH$_2$N$_3$ | i-C$_3$H$_7$ | O | 1 | |
| CH$_2$OCH$_3$ | 5,6,7,8 | 1 | CH$_2$CN | i-C$_3$H$_7$ | O | 2 | |
| ◁ | 8 | 1 | CH$_2$CN | i-C$_3$H$_7$ | O | 2 | |
| — | — | 0 | CH$_2$N$_3$ | CH$_3$ | O | 2 | 108 |
| — | — | 0 | CH$_2$—C(O)—NH—C(CH$_3$)$_3$ | i-C$_3$H$_7$ | O | 2 | 137 |
| — | — | 0 | CH$_2$—S—C(=S)—OCH$_3$ | i-C$_3$H$_7$ | O | 2 | 68 |
| — | — | 0 | CH$_2$—N=P(OCH$_3$)$_3$ | i-C$_3$H$_7$ | O | 2 | viscous oil |
| — | — | 0 | CH(CH$_3$)—S—C$_2$H$_5$ | i-C$_3$H$_7$ | O | 2 | n$_D^{20}$ = 1.5497 |
| — | — | 0 | CH$_2$—N(C$_6$H$_4$Cl)—COO—CH(CH$_3$)$_2$ | i-C$_3$H$_7$ | O | 2 | 129–132 |
| — | — | 0 | —C$_6$H$_5$ | i-C$_3$H$_7$ | O | 2 | 146–148 |

EXAMPLE 6

Herbicidal action of the new 2,1,3-benzothiadiazine compounds

Greenhouse experiments and experiments in the open were carried out in order to study the herbicidal and selective properties of the new compounds.

I. Greenhouse experiments

Plastic flowerpots having a volume of 300 cm$^3$ were filled with a sandy loam, and test plants were grown therein, separated by species.

The plants were either grown from seed, or from pregerminated tubers (e.g., *Cyperus esculentus*) or from transplanted vegetatively reproduced species. For the preemergence treatment, only seeds were suitable. The active ingredients were suspended or emulsified in water as distributing agent, and sprayed onto the surface of the soil by means of atomizing nozzles. After treatment, the vessels were lightly sprinkler-irrigated, and then covered with transparent plastic hoods until the plants emerged. In postemergence treatment (leaf treatment) the plants were first grown to a height of from 3 to 10 cm, depending on their habit, before being treated. The plants were of course not sprinkler-irrigated immediately, and no hoods were placed on the pots. The test plants were placed in either the cooler or warmer sections of the greenhouse, depending on their temperature requirements. The experimental period was from 2 to 4 weeks. During this period the plants were tended and their reactions to the various treatments were evaluated. The application rates of the compounds under investigation are given as kg of active ingredient per hectare. Assessment was on a 0 to 100 scale, 0 denoting no damage or normal emergence, and 100 denoting no emergence or destruction of the plants.

II. Experiments in the open

Here, postemergence treatments were carried out on small plots. The active ingredients were applied as an emulsion or suspension in water as carrier and distribution medium, with the aid of a motor-driven plot spray mounted on a hitch. All the experiments were observed for several weeks and also assessed on the 0 to 100 scale.

Results

The representatives of the new compounds listed in Tables 2 to 6 control unwanted plants better than the comparative agent 1-chloromethyl-3-isopropyl-2,1,3- benzothiadiazin-(4)-one-2,2-dioxide, and have an action similar to, and sometimes poorer than, that of comparative agent 3-isopropyl-2,1,3-benzothiadiazin-(4)-one-2,2-dioxide. Tolerance was in some crops the same as that of the comparative agents. However, in crops in which prior art agents from this class of compounds cannot be used, or only at considerable risk, such as potatoes, onions and sunflowers (these only being given by way of example), the compounds according to the invention proved to be far better tolerated; this is their value and the advance they represent.

TABLE 1

List of plant names

| Botanical name | Abbreviation in tables | English term |
|---|---|---|
| *Abutilon theophrastii* | Abut. theo. | velvet leaf |
| *Allium cepa* | — | onion |
| *Amaranthus spp.* | Amar. spp. | pigweed |
| *Ammania coccinea* | Amman. cocc. | redstem |
| *Chenopodium spp.* | Chenop. spp. | lambsquarters |
| *Chrysanthemum segetum* | Chrys. seget. | corn marigold |
| *Cucumis sativus* | Cucumis sat. | cucumber |

TABLE 1-continued

List of plant names

| Botanical name | Abbreviation in tables | English term |
|---|---|---|
| *Cyperus esculentus* | Cyper. escul. | yellow nutsedge |
| *Datura stramonium* | Datura stram. | Jimsonweed |
| *Galium aparine* | Gali. apar. | catchweed bedstraw |
| *Galinsoga spp.* | Galins. app. | gallant soldier |
| *Glycine max* | — | soybean |
| *Helianthus annuus* | Helianth. annuus | sunflower |
| *Hordium vulgare* | Hord. vulg. | barley |
| *Laminum spp.* | — | deadnettle |
| *Matricaria spp.* | Matric. spp. | chamomile |
| *Medicago sativa* | Medic. sat. | alfalfa |
| *Mentha piperita* | Mentha pip. | peppermint |
| *Oryza sativa* | Oryza sat. | rice |
| *Phaseolus vulgaris* | Phaseol. vulg. | snapbean |
| *Raphanus spp.* | — | wild radish |
| *Sida spinosa* | Sida spin. | prickly sida |
| *Sinapis spp.* | — | yellow charlock |
| *Solanum nigrum* | Solan. nigr. | black nightshade |
| *Solanum tuberosum* | Solan. tub. | potato |
| *Stellaria media* | Stell. med. | chickweed |
| *Zea mays* | — | Indian corn |

TABLE 2

Selective herbicidal action in vegetables; postemergence treatment in the greenhouse Basic molecule 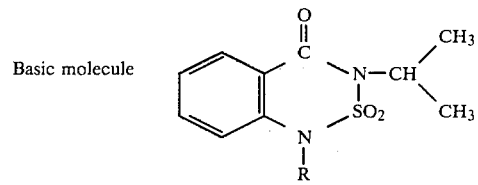

| Compound no. | Substituent R | Application rate kg/ha | Allium cepa | Cucumis sat. | Phaseol. vulg. | Abut. theo. | Datura stram. | Lamium spp. | Solan. nigr. | Stell. med. |
|---|---|---|---|---|---|---|---|---|---|---|
| 1 | —CH₂—C≡CH | 0.5 | 10 | 0 | 0 | 78 | 95 | 80 | 57 | 83 |
|   |   | 1.0 | 20 | 0 | 0 | 82 | — | 80 | 80 | 97 |
|   |   | 2.0 | 25 | 0 | 0 | 88 | — | 100 | 93 | 97 |
| 2 | —CH₂—CN | 0.5 | 0 | 0 | 0 | 98 | 100 | 80 | 82 | 70 |
|   |   | 1.0 | 10 | 0 | 0 | 98 | — | 100 | 82 | 100 |
|   |   | 2.0 | 20 | 10 | 0 | 98 | — | — | 98 | 100 |
| 3 | —CH₂—Cl (prior art) | 0.5 | 30 | 0 | 0 | 48 | 95 | 60 | 20 | 58 |
|   |   | 1.0 | 32 | 0 | 0 | 52 | — | 60 | 20 | 80 |
|   |   | 2.0 | 40 | 0 | 0 | 52 | — | 100 | 40 | 95 |
| 4 | H (prior art) | 0.5 | 63 | 0 | 0 | 68 | 100 | 50 | 88 | 82 |
|   |   | 1.0 | 65 | 5 | 0 | 72 | — | 50 | 92 | 88 |
|   |   | 2.0 | 65 | 10 | 0 | 78 | — | 100 | 98 | 95 |

0 = no damage
100 = plants destroyed

TABLE 3

Selective herbicidal action in sunflowers and other crops; postemergence treatment in the greenhouse Basic molecule 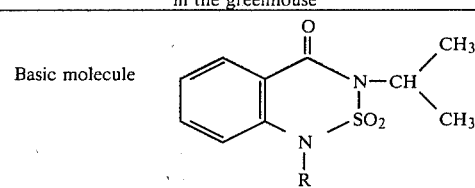

| Compound no. | Substituent R | Application rate kg/ha | Helianth. annuus | Hord. vulg. | Zea mays | Datura stram. | Sida spin. | Stell. med. |
|---|---|---|---|---|---|---|---|---|
| 5 | —CH₂—C₆H₅ | 2.0 | 0 | 0 | 5 | 95 | 95 | 65 |
|   |   | 4.0 | 5 | 0 | 10 | — | — | — |
| 4 | H | 2.0 | 100 | 0 | 0 | 100 | 93 | 95 |
|   |   | 4.0 | 100 | 0 | 7 | — | — | — |
| 6 | —CH₂—CH=CH₂ | 2.0 | 0 | 0 | 0 | 95 | — | 50 |
|   |   | 4.0 | 10 | 0 | 0 | — | — | — |
| 7 | —CH₂—CH₂—CH₃ | 2.0 | 0 | 0 | 0 | 95 | — | 80 |

TABLE 3-continued

Selective herbicidal action in sunflowers and other crops; postemergence treatment in the greenhouse Basic molecule: benzothiadiazinone with N—CH(CH$_3$)$_2$ substituent and N—R

| Compound no. | Substituent R | Application rate kg/ha | Helianth. annuus | Hord. vulg. | Zea mays | Datura stram. | Sida spin. | Stell. med. |
|---|---|---|---|---|---|---|---|---|
| | | 4.0 | 0 | 0 | 12 | — | — | — |

0 = no damage
100 = plants destroyed

TABLE 4

Action and selectivity; postemergence treatment in the greenhouse

Basic molecule: benzothiadiazinone with N—C$_3$H$_7$i and N—R

| Compound no. | Substituent R | Application rate kg/ha | Hord. vulg. | Medic. sat. | Mentha. pip. | Oryza sat. | Zea mays | Amar. spp. | Amman. cocc. | Cyper. escul. | Chenop. spp. | Chrys. seget. | Galium apar. | Matri. spp. |
|---|---|---|---|---|---|---|---|---|---|---|---|---|---|---|
| 8 | —CH$_2$—N$_3$ | 0.5 | 0 | — | 0 | 0 | 0 | 100 | 10 | 33 | 100 | 100 | 33 | 100 |
| | | 1.0 | 0 | 0 | 0 | 0 | 0 | 100 | 70 | 32 | 100 | 100 | 82 | 100 |
| | | 4.0 | 0 | 0 | 0 | 8 | 0 | — | — | 42 | — | — | 95 | 100 |
| 9 | —CH$_2$—SCN | 0.5 | 0 | — | — | 0 | 0 | 15 | 95 | 50 | — | 100 | — | 100 |
| | | 1.0 | 0 | — | — | 0 | 10 | 20 | 95 | 60 | — | 100 | — | 100 |
| | | 4.0 | 0 | — | — | 20 | 10 | — | — | 95 | — | — | — | — |
| 3 | —CH$_2$Cl | 0.5 | — | — | 0 | 0 | 5 | 75 | — | 10 | — | 92 | 10 | 100 |
| | | 1.0 | — | 0 | 0 | 0 | 5 | 75 | — | 15 | — | 98 | 60 | 100 |
| | | 4.0 | — | 20 | 0 | 0 | 10 | — | — | 35 | — | — | — | — |
| 4 | H | 0.5 | 0 | — | 0 | 0 | 0 | 23 | 85 | 26 | 100 | 99 | 50 | 100 |
| | | 1.0 | 0 | 0 | 0 | 0 | 0 | 43 | 88 | 34 | 100 | 99 | 60 | 100 |
| | | 4.0 | 0 | 20 | 0 | 0 | 7 | — | — | 60 | — | — | — | — |

100 = plants destroyed
0 = no action

TABLE 5

Selective herbicidal action; postemergence treatment in the open

| Compound no. | Application rate kg/ha | Glyc. max. | Solan. tub. | Zea mays | Chenop. spp. | Galins. spp. | Gali. apar. | Sinapis/ Raphanus |
|---|---|---|---|---|---|---|---|---|
| 8 | 2.0 | 5 | 4 | 0 | 94 | 95 | 88 | 100 |
| 9 | 1.0 | 2 | — | 0 | 86 | 92 | — | 100 |
| | 2.0 | 5 | — | — | — | — | — | — |
| 2 | 1.0 | 10 | — | 0 | 53 | 13 | 100 | 90 |
| | 2.0 | — | — | — | 75 | 20 | 100 | 90 |
| 4 | 2.0 | 6 | 14 | 0 | 90 | 95 | 88 | 100 |

0 = no damage
100 = plants destroyed

TABLE 6

Pre- and postemergence treatment with new 2,1,3-benzothiadiazine derivatives in the greenhouse Basic molecule:

```
         O
         ||
    [benzene ring]—C—N—C3H7i
                    |
                    SO2
                    |
                    N
                    |
                    R
```

| Compound no. | Substituent | kg/ha | Method | Test plant and % damage Sida spinosa |
|---|---|---|---|---|
| 10 | —CH2—C(=S)NH2 | 1.0 | pre | 95 |
|    |               | 2.0 | pre | 95 |
|    |               | 1.0 | post | 95 |
|    |               | 2.0 | post | 95 |
| 4  | —H            | 1.0 | pre | 60 |
|    |               | 2.0 | pre | 60 |
|    |               | 1.0 | post | 95 |
|    |               | 2.0 | post | 95 |
| 8  | —CH2—N3       | 1.0 | pre | 80 |
|    |               | 2.0 | pre | 92 |
|    |               | 1.0 | post | 78 |
|    |               | 2.0 | post | 95 |

0 = no damage
100 = plants destroyed
pre = preemergence treatment
post = postemergence treatment

TABLE 7

Biological action of new 2,1,3-benzothiadiazine derivatives on *Sinapis alba*; postemergence treatment in the greenhouse

```
         O
         ||
    X—[benzene ring]—C—N—R2
                       |
                       SO2
                       |
                       N
                       |
                       R1
```

| Compound no. | Substituents R1 | R2 | X | Ring position | kg/ha | Sinapis alba and % damage |
|---|---|---|---|---|---|---|
| | —CH2S—P(=O)(OC2H5)(NHC3H7i) | C3H7i | H | — | 2.0 | 100 |
| | —CH2—C≡CH | C4H9sec | H | — | 2.0 | 100 |
| | —CH2—CH2Br | C3H7i | H | — | 2.0 | 75 |
| | —CH2—C≡CCH2Cl | C3H7i | H | — | 2.0 | 90 |
| | —CH(CCl3)—NH—C(=O)—H | C3H7i | H | — | 2.0 | 100 |
| | —CH2COCH3 | C3H7i | H | — | 2.0 | 90 |
| | —CH2CH2—C(=O)—CH3 | C3H7i | H | — | 2.0 | 100 |
| | —CH2CH2CN | C3H7i | H | — | 2.0 | 100 |
| | —CH2CH2C(=O)NH2 | C3H7i | H | — | 2.0 | 100 |
| | —CH2NH—C(=O)—CH2Cl | C3H7i | H | — | 2.0 | 100 |
| | —CH2S—C(=S)—N(C2H5)2 | C3H7i | H | — | 2.0 | 100 |
| | —CH2S—C(=S)—N(C3H7i)2 | C3H7i | H | — | 2.0 | 100 |
| | —CH2S—C(=S)—N(C2H5)(C4H9n) | C3H7i | H | — | 2.0 | 80 |
| | CH2S—C(=S)—N(piperidine-2-CH3) | C3H7i | H | — | 2.0 | 100 |
| | CH2S—C(=S)—N(CH3)(C(CH3)2CH3) | C3H7i | H | — | 2.0 | 100 |

TABLE 7-continued

Biological action of new 2,1,3-benzothiadiazine derivatives on *Sinapis alba*; postemergence treatment in the greenhouse Structure: benzene ring with X substituent, C(=O)-N(R²)-SO₂-CH₂-N(R¹) ring system

| Compound no. | Substituents R¹ | R² | X | Ring position | kg/ha | *Sinapis alba* and % damage |
|---|---|---|---|---|---|---|
| | $CH_2-S-C(=S)-OC_2H_5$ | $C_3H_7i$ | H | — | 2.0 | 100 |
| | $CH_2-N=P(OC_2H_5)_3$ | $C_3H_7i$ | H | — | 2.0 | 100 |
| | $CH_2C\equiv CH$ | $C_3H_7i$ | Cl | 7 | 2.0 | 100 |
| | $CH_2C\equiv CH$ | $C_3H_7i$ | Cl | 8 | 2.0 | 80 |
| | $-CH_2-N_3$ | $CH_3$ | H | — | 2.0 | 100 |
| | $-CH_2-S-C(=S)-O-CH_3$ | $C_3H_7i$ | H | — | 2.0 | 100 |
| | $-CH_2-N=P(OCH_3)_3$ | $C_3H_7i$ | H | — | 2.0 | 100 |
| | $-CH(CH_3)-S-C_2H_5$ | $C_3H_7i$ | H | — | 2.0 | 100 |

0 = no damage
100 = plants destroyed

The new active ingredients may be used for controlling unwanted plant growth in the following crops:

| Botanical name | English term |
|---|---|
| *Ananas comosus* | pineapple |
| *Arachis hypogaea* | peanuts (groundnuts) |
| *Asparagus officinalis* | asparagus |
| *Avena sativa* | oats |
| *Beta vulgaris* spp. *altissima* | sugarbeet |
| *Beta vulgaris* spp. *rapa* | fodder beet |
| *Beta vulgaris* spp. *esculenta* | table beet, red beet |
| *Brassica napus* var. *napus* | rape |
| *Brassica napus* var. *napobrassica* | |
| *Brassica napus* var. *rapa* | turnips |
| *Brassica rapus* var. *silvestris* | |
| *Camellia sinensis* | tea plants |
| *Carthamus tinctorius* | safflower |
| *Citrus limon* | lemon |
| *Citrus maxima* | grapefruit |
| *Citrus reticulata* | |
| *Citrus sinensis* | orange trees |
| *Caffea arabica* (*Coffea canephora*, *Coffea liberica*) | coffee plants |
| *Cucumis melo* | melons |
| *Cynodon dactylon* | Bermudagrass in turf and lawns |
| *Daucus carota* | carrots |
| *Elaeis guineensis* | oil palms |
| *Fragaria vesca* | strawberries |
| *Gossypium hirsutum* (*Gossypium arboreum* *Gossypium herbaceum* *Gossypium vitifolium*) | cotton |
| *Helianthus tuberosus* | |
| *Hevea brasiliensis* | rubber plants |
| *Humulus lupulus* | hops |
| *Iopmoea batatas* | sweet potatoes |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Musa* spp. | banana plants |
| *Nicotiana tabacum* (*N. rustica*) | tobacco |
| *Olea europaea* | olive trees |
| *Panicum miliaceum* | |
| *Phaseolus lunatus* | limabeans |
| *Phaseolus mungo* | mungbeans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus persica* | peach trees |
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* rye | |
| *Sesamum indicum* | Sesame |
| *Sorghum bicolor* (s. *vulgare*) | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |

To further increase the spectrum of action of the new individual active ingredients, to achieve synergistic effects or to improve persistence in the soil, numerous other herbicidal compounds and growth regulators may be used as components for mixtures and combination. Depending on the area of use and the unwanted plants to be controlled, the following substances or similar derivatives are suitable as components:

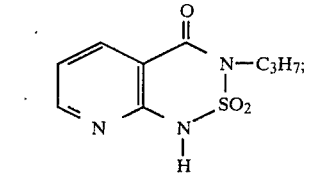

and salts

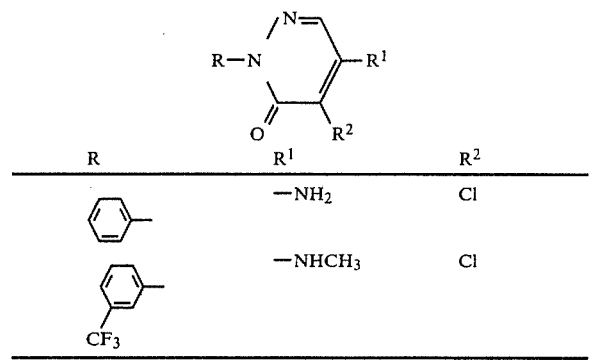

| R | R¹ | R² |
|---|----|----|
| phenyl | —NH₂ | Cl |
| 3-CF₃-phenyl | —NHCH₃ | Cl |

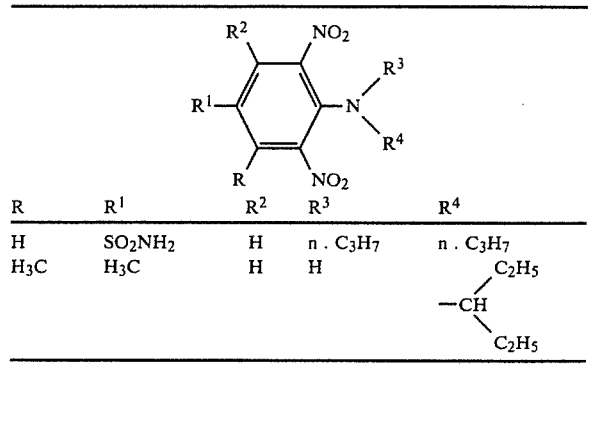

| R | R¹ | R² | R³ | R⁴ |
|---|----|----|----|----|
| H | SO₂NH₂ | H | n.C₃H₇ | n.C₃H₇ |
| H₃C | H₃C | H | H | —CH(C₂H₅)₂ |

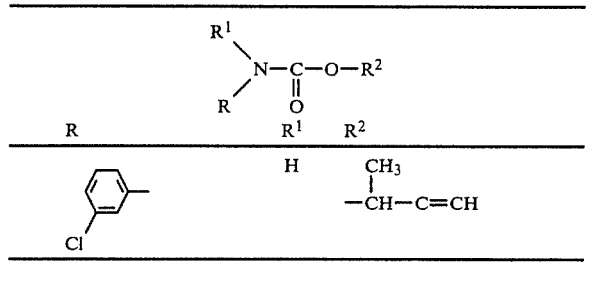

| R | R¹ | R² |
|---|----|----|
| 3-Cl-phenyl | H | —CH(CH₃)—C≡CH |

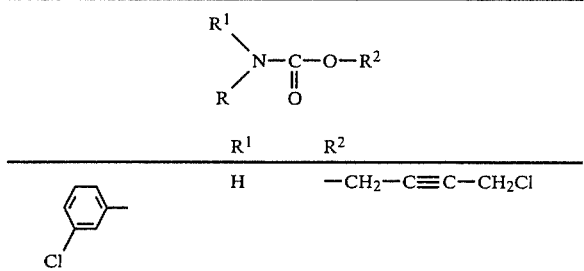

| R | R¹ | R² |
|---|----|----|
| 3-Cl-phenyl | H | —CH₂—C≡C—CH₂Cl |

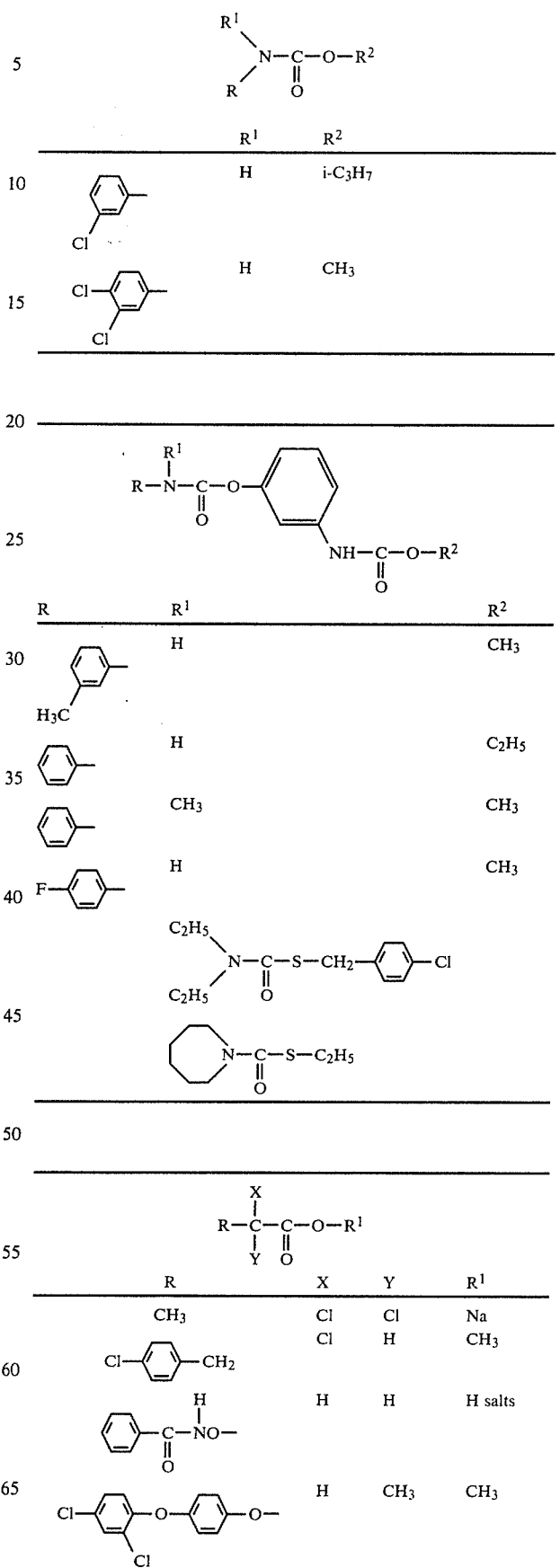

-continued $$R^1\text{-}N(R)\text{-}C(=O)\text{-}O\text{-}R^2$$

| R | R¹ | R² |
|---|----|----|
| 3-Cl-phenyl | H | i-C₃H₇ |
| 3,4-diCl-phenyl | H | CH₃ |

$$R\text{-}N(R^1)\text{-}C(=O)\text{-}O\text{-}phenyl\text{-}NH\text{-}C(=O)\text{-}O\text{-}R^2$$

| R | R¹ | R² |
|---|----|----|
| 3-CH₃-phenyl | H | CH₃ |
| phenyl | H | C₂H₅ |
| phenyl | CH₃ | CH₃ |
| 4-F-phenyl | H | CH₃ |

(C₂H₅)₂N—C(=O)—S—CH₂—C₆H₄—Cl(4)

azepan-1-yl—C(=O)—S—C₂H₅

$$R\text{-}C(X)(Y)\text{-}C(=O)\text{-}O\text{-}R^1$$

| R | X | Y | R¹ |
|---|---|---|----|
| CH₃ | Cl | Cl | Na |
| 4-Cl-C₆H₄-CH₂ | Cl | H | CH₃ |
| C₆H₅—C(=O)—N(H)—O— | H | H | H salts |
| 2,4-diCl-C₆H₃-O-C₆H₄-O- | H | H | CH₃ CH₃ |

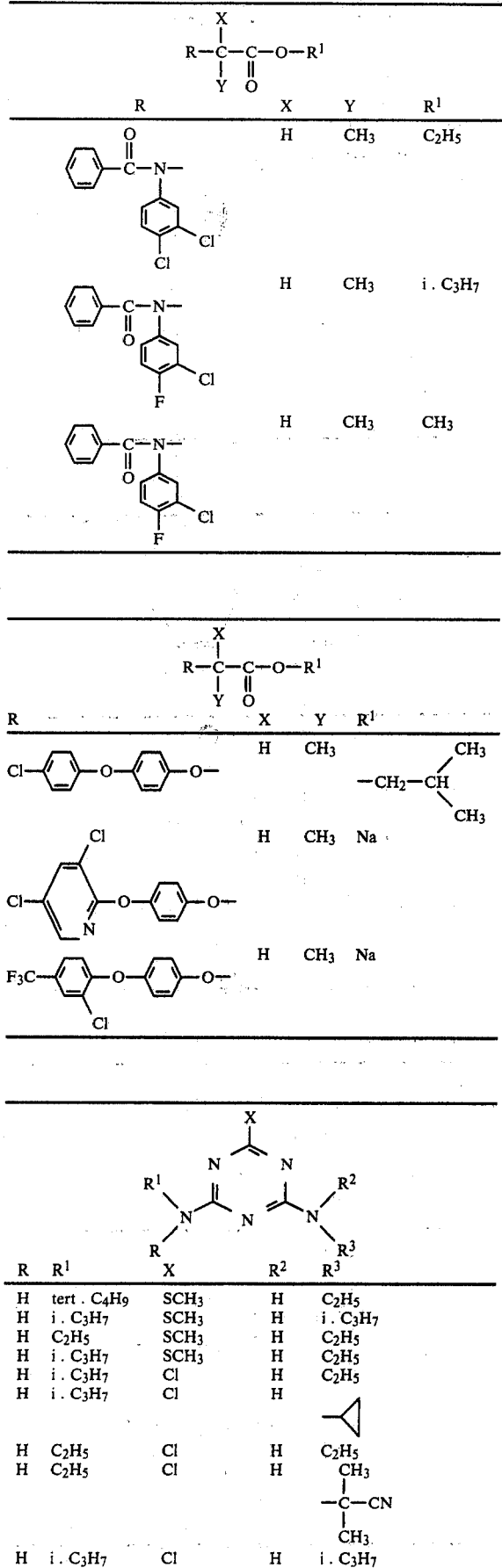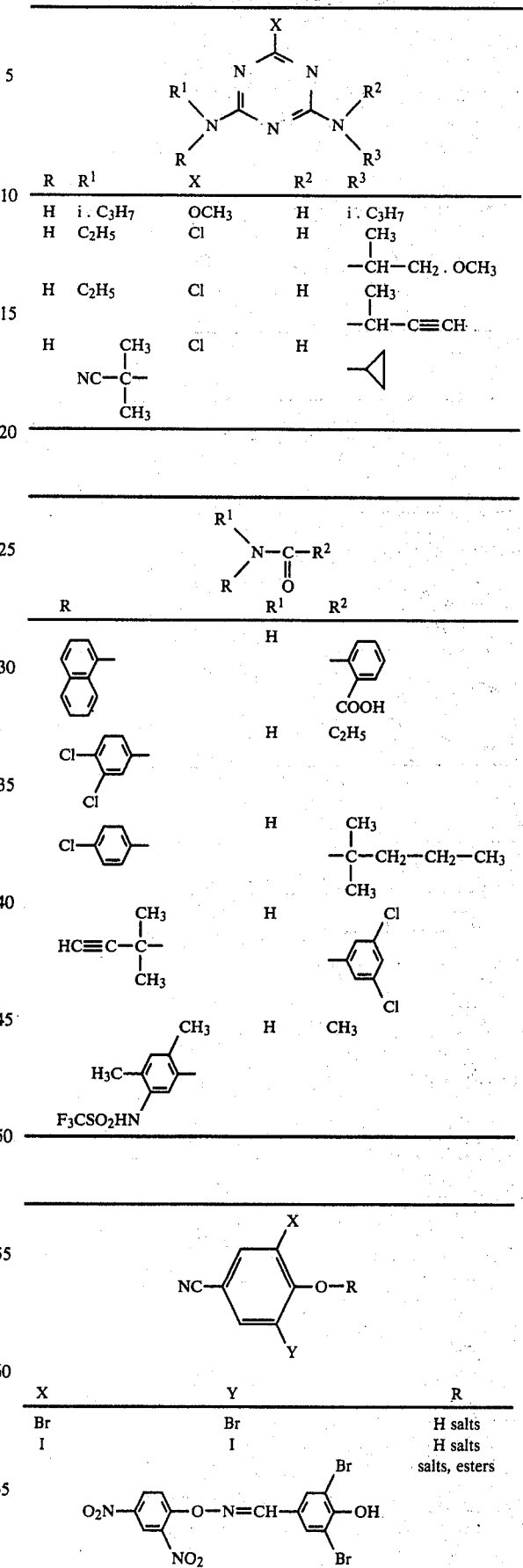

-continued
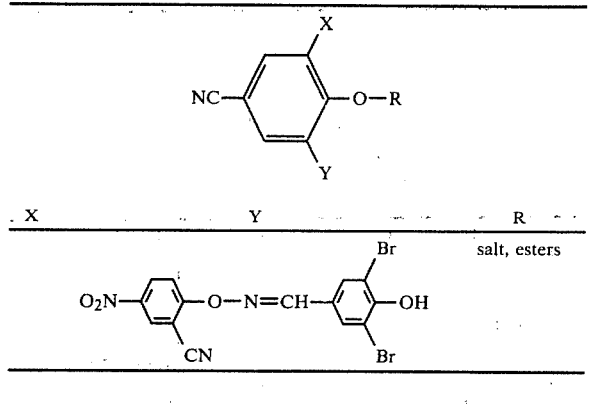
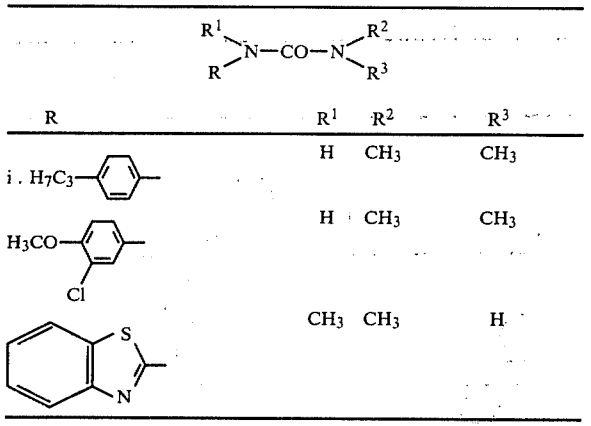
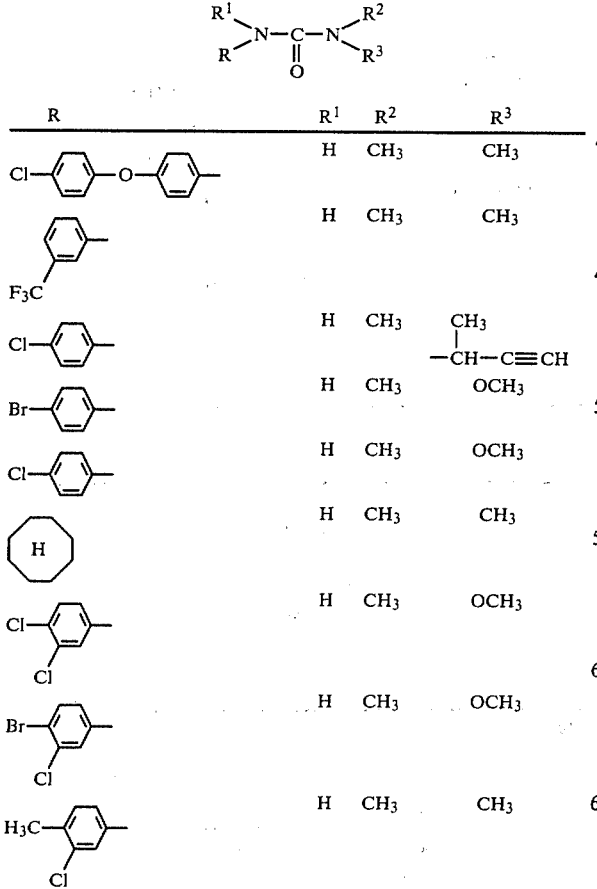
-continued
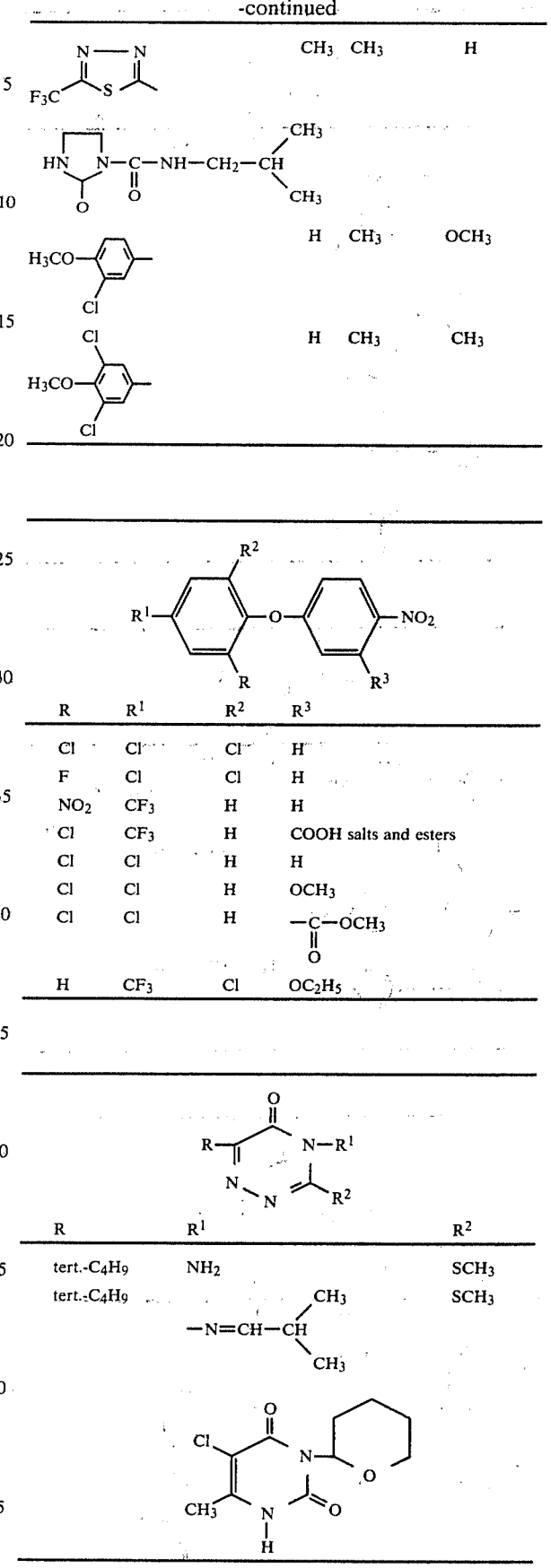

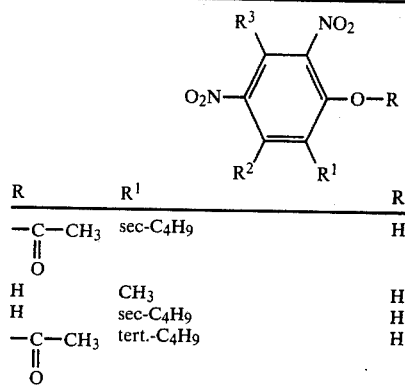
| R | R¹ | R² | R³ |
|---|---|---|---|
| —C(=O)—CH₃ | sec-C₄H₉ | H | H |
| H | CH₃ | H | H salts, esters |
| H | sec-C₄H₉ | H | H salts, esters |
| —C(=O)—CH₃ | tert.-C₄H₉ | H | H |
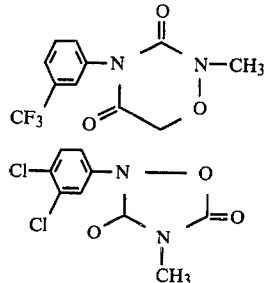
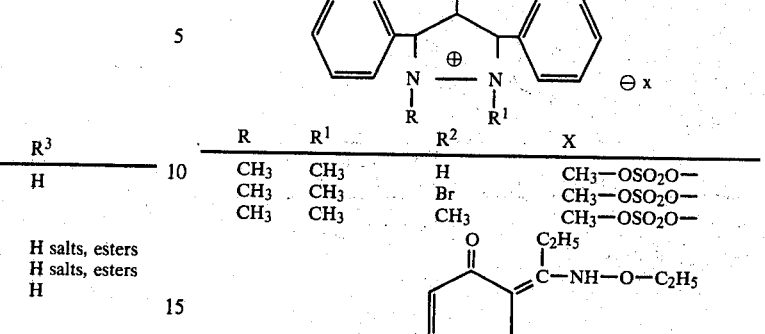
| R | R¹ | R² | X |
|---|---|---|---|
| CH₃ | CH₃ | H | CH₃—OSO₂O— |
| CH₃ | CH₃ | Br | CH₃—OSO₂O— |
| CH₃ | CH₃ | CH₃ | CH₃—OSO₂O— |
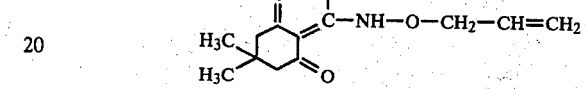
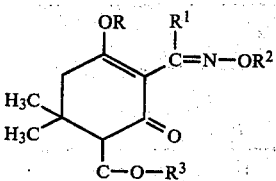
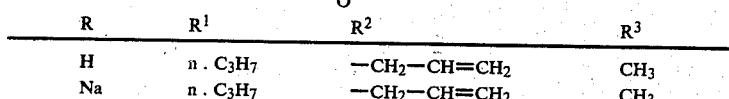
| R | R¹ | R² | R³ |
|---|---|---|---|
| H | n-C₃H₇ | —CH₂—CH=CH₂ | CH₃ |
| Na | n-C₃H₇ | —CH₂—CH=CH₂ | CH₃ |
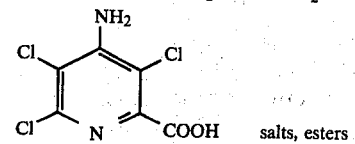
salts, esters
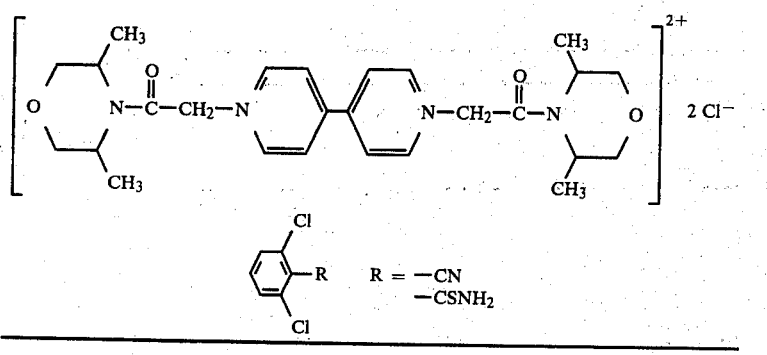

It is also possible to apply the new compounds according to the invention, either alone or in combination with other herbicides, in admixture with further crop protection agents, e.g., agents for combatting pests, or phytopathogenic fungi or bacteria. Of further interest is the miscibility of the compounds with mineral salt solutions used to eliminate nutritional or trace element deficiencies.

Spreader-stickers are nonphytotoxic oils may be added to ensure the herbicidal action.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. Application rates vary from 0.1 to 10, especially from 0.5 to 5, kg of active ingredient per hectare.

EXAMPLE 7

90 parts by weight of compound 1 is mixed with 10 parts by weight of N-methyl-α-pyrrolidone. A mixture is obtained which is suitable for application in the form of very fine drops.

EXAMPLE 8

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 5 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 1 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound 2 is intimately mixed with 97 parts by weight of particulate kaolin. A dust is obtained containing 3% by weight of the active ingredient.

EXAMPLE 13

30 parts by weight of compound 5 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

40 parts by weight of compound 6 is intimately mixed with 10 parts of the sodium salt of a phenolsulfonic acid-urea-formaldehyde condensate, 2 parts of silica gel and 48 parts of water. A stable aqueous dispersion is obtained. Dilution in 100,000 parts by weight of water gives an aqueous dispersion containing 0.04 wt% of active ingredient.

EXAMPLE 15

20 parts of compound 1 is intimately mixed with 2 parts of the calcium salt of dodecylbenzenesulfonic acid, 8 parts of a fatty alcohol polyglycol ether, 2 parts

We claim:
1. A compound of the formula

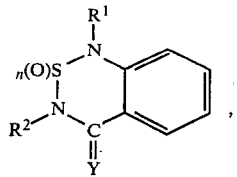

where R¹ is lower alkynyl; lower haloalkenyl; lower haloalkynyl; lower alkoxycarboalkyl; lower alkoxycarboalkenyl; lower alkanoylalkyl; lower azidoalkyl; lower thiocyanatoalkyl; lower cyanoalkyl; carbamyl-lower alkyl; carbamyl-lower alkyl substituted by halogen; halo- or methyl substituted phenyl; lower alkylmercaptoalkyl, lower phenylmercaptoalkyl, wherein in said alkylmercaptoalkyl and phenylmercaptoalkyl the final alkyl has more than 1 carbon atom; or methyl substituted by lower O-alkyl-N-alkylaminophosphorothio, lower O,O-dialkylphosphoro, lower O,O,O-trialkylphosphinylimino, lower alkoxy thiocarbonyl thio, lower alkylsulfinyl, thiocarbamido, isothiuronium hydrochloride,

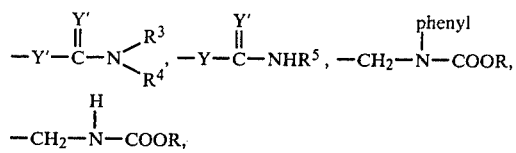

lower alkanoylamido, lower alkanoylamido substituted by halogen, phthalylimidoalkyl, isoxazole or isoxazole substituted by methyl or halogen;
R² is isopropyl;
n is 2;
R and R³ are lower alkyl,
R⁴ is lower alkyl or hydrogen,
R⁵ is lower alkyl or phenyl; and
each Y and Y' independently is oxygen or sulfur.

2. 1-propargyl-3-isopropyl-2,1,3-benzothiadiazin-(4)-one-2,2-dioxide.
3. 1-azidomethyl-3-isopropyl-2,1,3-benzothiadiazin-(4)-one-2,2-dioxide.
4. 1-thiocyanatomethyl-3-isopropyl-2,1,3-benzothiadiazin-(4)-one-2,2-dioxide.
5. 1-cyanomethyl-3-isopropyl-2,1,3-benzothiadiazin-(4)-one-2,2-dioxide.
6. 1-thiocarbamidomethyl-3-isopropyl-2,1,3-benzothiadiazin-(4)-one-2,2-dioxide.
7. 1-methyl-(O-ethyl-N-isopropylaminophosphorothio)-3-isopropyl-2,1,3-benzothiadiazin-(4)-one-2,2-dioxide.
8. 1-propargyl-3-sec-butyl-2,1,3-benzothiadiazin-(4)-one-2,2-dioxide.

* * * * *

UNITED STATES PATENT AND TRADEMARK OFFICE
CERTIFICATE OF CORRECTION

PATENT NO. : 4,298,731

DATED : November 3, 1981

INVENTOR(S) : G. Hamprecht, G. Stubenrauch, H. Urbach, and B. Wuerzer

It is certified that error appears in the above—identified patent and that said Letters Patent is hereby corrected as shown below:

On the cover page, following "Attorney, Agent, or Firm", delete "Lee" and insert --Keil-- in its place so that it reads --Keil & Witherspoon--.

Signed and Sealed this

Sixth Day of April 1982

[SEAL]

Attest:

Attesting Officer

GERALD J. MOSSINGHOFF

Commissioner of Patents and Trademarks